US010379046B2

(12) United States Patent
Katzlinger et al.

(10) Patent No.: US 10,379,046 B2
(45) Date of Patent: Aug. 13, 2019

(54) METHOD AND SYSTEM FOR MULTIPLEXED TIME-RESOLVED FLUORESCENCE DETECTION

(71) Applicant: Molecular Devices, LLC, Sunnyvale, CA (US)

(72) Inventors: Michael Katzlinger, Eugendorf (AT); Evan F. Cromwell, Redwood City, CA (US); Vanitha Thulasiraman, San Jose, CA (US)

(73) Assignee: Molecular Devices, LLC, San Jose, CA (US)

( * ) Notice: Subject to any disclaimer, the term of this patent is extended or adjusted under 35 U.S.C. 154(b) by 161 days.

(21) Appl. No.: 14/682,026

(22) Filed: Apr. 8, 2015

(65) Prior Publication Data
US 2016/0299076 A1 Oct. 13, 2016

(51) Int. Cl.
*G01N 21/64* (2006.01)

(52) U.S. Cl.
CPC . *G01N 21/6408* (2013.01); *G01N 2021/6419* (2013.01); *G01N 2021/6421* (2013.01); *G01N 2021/6441* (2013.01); *G01N 2201/0245* (2013.01)

(58) Field of Classification Search
None
See application file for complete search history.

(56) References Cited

U.S. PATENT DOCUMENTS

| 4,474,892 | A | * | 10/1984 | Murad | G01N 33/54306 436/513 |
| 4,659,678 | A | * | 4/1987 | Forrest | G01N 33/54306 436/512 |
| 6,537,829 | B1 | | 3/2003 | Zarling et al. | |
| 2004/0265938 | A1 | * | 12/2004 | Remacle | C12Q 1/42 435/7.92 |
| 2007/0287709 | A1 | * | 12/2007 | Goutopoulos | C07D 213/79 514/236.5 |
| 2008/0138830 | A1 | * | 6/2008 | De Pauw | G01N 33/74 435/7.1 |
| 2009/0142856 | A1 | | 6/2009 | Hudack et al. | |
| 2010/0035349 | A1 | | 2/2010 | Bau et al. | |
| 2010/0184046 | A1 | * | 7/2010 | Klass | C12Q 1/6886 435/7.1 |
| 2013/0150265 | A1 | | 6/2013 | Balog et al. | |
| 2013/0162981 | A1 | * | 6/2013 | Emeric | G01N 33/48 356/72 |

FOREIGN PATENT DOCUMENTS

WO 2013184168 A1 12/2013

OTHER PUBLICATIONS

Song et al. Time-resolved lanthanide luminescence for lab-on-chip detection of biomarkers on cancerous tissue, Analyst, 132, (2009), p. 1991-1993.*
Uniprot, "UniprotKB-P25103 (NK1R_HUMAN)". Sep. 21, 2011. Online. http://www.uniprot.org/uniprot/P25103. Accessed via the Internet Archive. [https://web.archive.org/web/20111007170859/http://www.uniprot.org/uniprot/P25103] on May 25, 2016.*
Sloviter et al. Substance P Receptor Expression by Inhibitory Interneurons of the Rat Hippocampus: Enhanced Detection Using Improved Immunocytochemical Methods for the Preservation and Colocalization of GABA and Other Neuronal Markers, The Journal of Comparative Neurology, 430, (2001), p. 283-305.*
Geddes, Chris D. Reviews in Fluorescence 2009. New York: Springer, (2011). Print. (Year: 2011).*
International Search Report and Written Opinion for PCT/US2016/019563 dated Jun. 30, 2016.

* cited by examiner

*Primary Examiner* — Bao Thuy L Nguyen
*Assistant Examiner* — Ellen J Marcsisin

(57) ABSTRACT

The present invention is directed to a novel method to multiplex long lifetime fluorescent dyes using time-resolved fluorescence (TRF) detection. A combination of spectral and temporal differences in fluorescence emission is used to enhance the ability to separate signals in an assay from multiple dyes. Multiplexed TRF detection apparatuses and systems configured for performing all or part of any of the methods disclosed herein are also provided, particularly apparatuses and systems incorporating cartridge-based multi-mode readers.

21 Claims, 19 Drawing Sheets

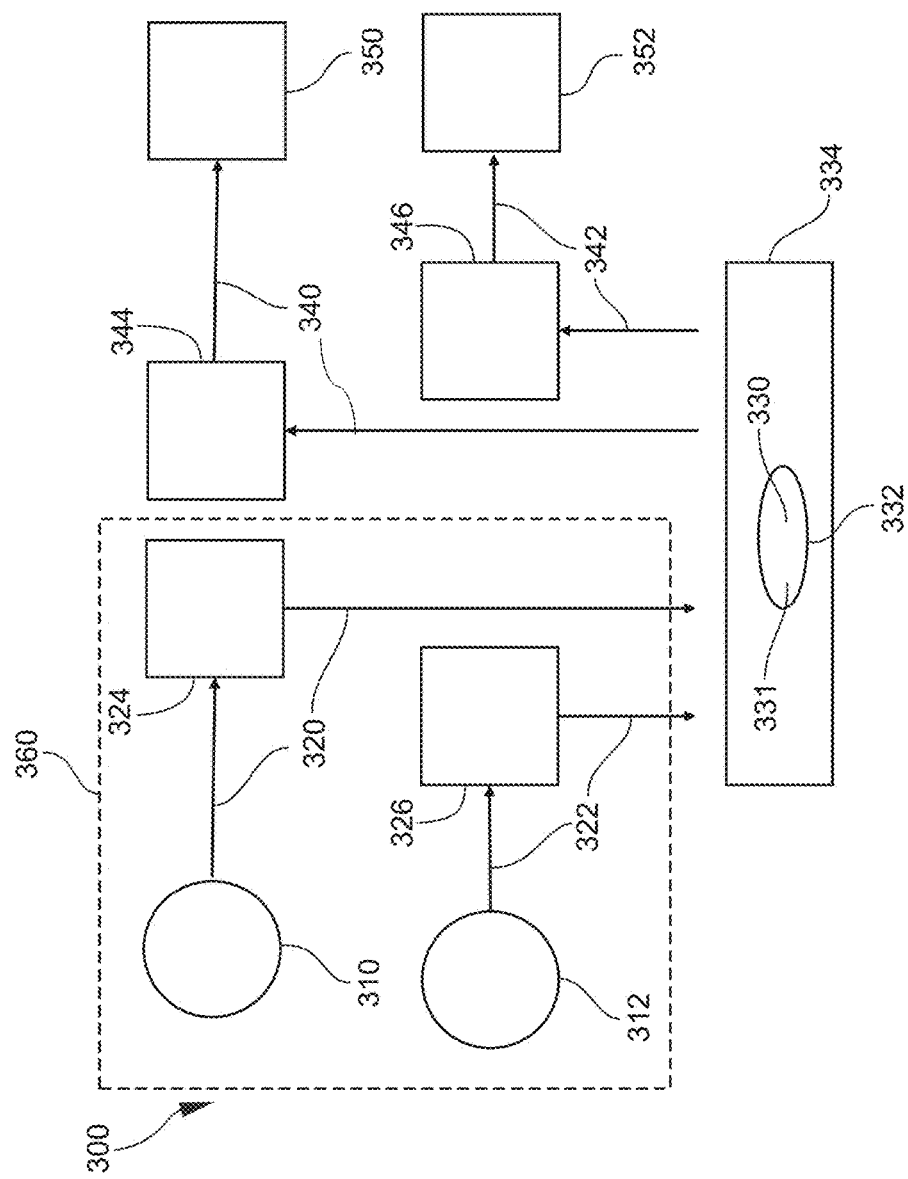

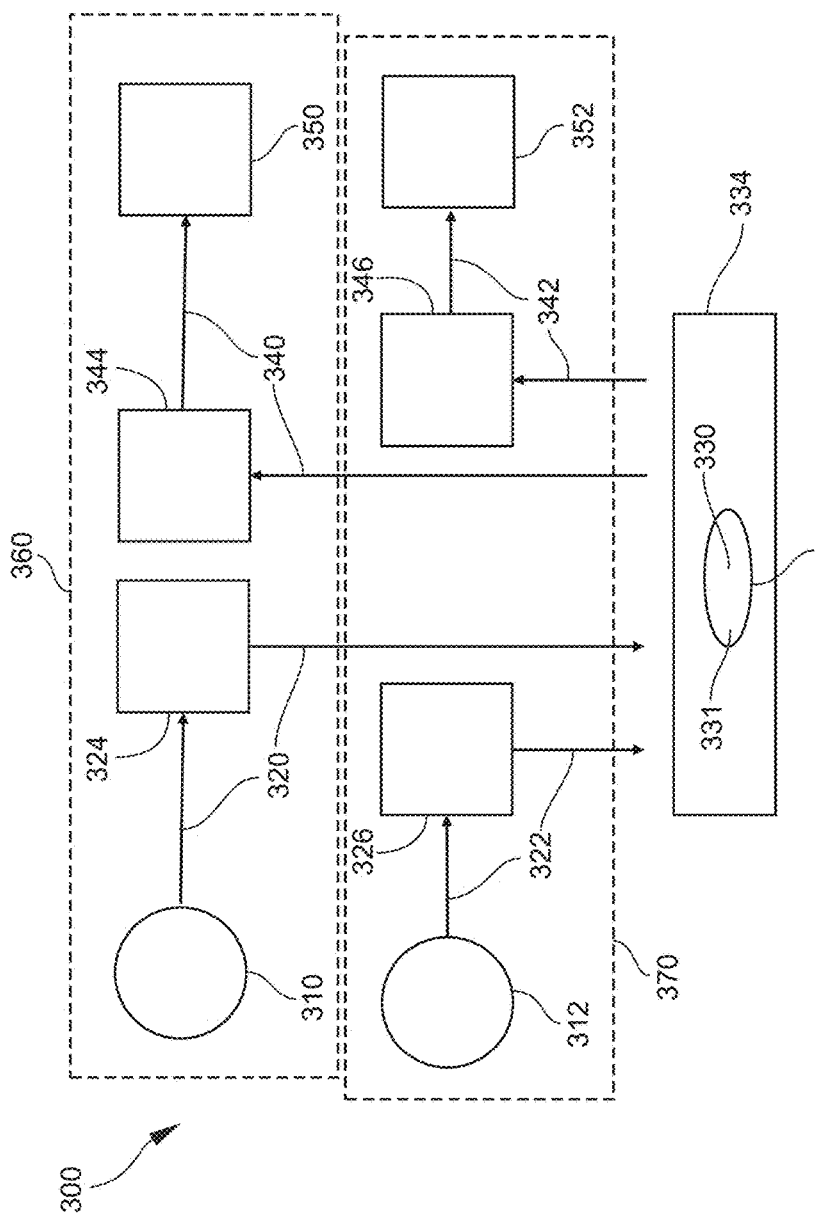

METHOD AND SYSTEM FOR MULTIPLEXED TIME-RESOLVED FLUORESCENCE DETECTION

TECHNICAL FIELD

The present invention generally relates to a multiplexed time-resolved fluorescence (TRF) detection method and system, and particularly a multiplexed system that maintains the high sensitivity, background rejection, stability, resistance to photo bleaching, and dynamic range of time-resolved fluorescence detection with minimal or no cross talk between channels.

BACKGROUND

Protein detection and characterization is an important task for pharmaceutical and clinical research. Chemiluminescence (CL) is a common method for detection of proteins in biochemical analyses or on surface-bound and spatially separated proteins. An example of the latter is the method of sodium dodecyl sulfate-polyacrylamide gel electrophoresis (SDS-PAGE) with electrophoretic transfer of proteins to a membrane, referred to as Western Blot (WB) analysis (Towbin et al. (1979) Proc. Natl. Acad. Sci. U.S.A. 76(9):4350-4354; Renart et al. (1979) Proc. Natl. Acad. Sci. U.S.A. 76(7):3116-3120). Electro-chemiluminescence (ECL) has also been applied to detect proteins bound to spots in specially designed multiwell plates (e.g., MULTI SPOT® and MULTI-ARRAY™ plates and SECTOR™ instruments, Meso Scale Discovery, a division of Meso Scale Diagnostics, LLC, Gaithersburg, Md.).

An advantage of CL and ECL is very high sensitivity with limits of detection for proteins in solution in the sub-picogram/ml range. However, these systems produce transient signals, are not chemically stable, and require a complicated procedure to produce the chemical reaction required for detection. They are also non-linear systems (i.e., one probe produces many photons) and have poor reproducibility so are not suitable for applications where quantitation of protein amount is desired. A last, but significant limitation is the inability to multiplex multiple CL signals. Their emissions are very broad and that makes the ability to detect two different CL emissions from the same spatial location very challenging.

Fluorescence (FL) probes overcome some of the limitations of CL. They provide ability for better quantitation since the relationship between excitation photons and emission photons is, in general, linear. They are also more versatile as there is no need to provide access to the probes by other reactive molecules. In general, FL probes are also more stable, especially when protected from light as they are generally non-reactive chemical species. Perhaps the most important advantage of FL probes is that they provide the ability to perform multiplexing. FL molecules come in a wide variety of forms with a wide range of excitation and emission bands. Thus two (or more) probes at the same spatial location can be independently excited and detected with minimal overlap (or cross-talk) between detection channels. The ability to detect up to four independent fluorophores from the same spatial location is regularly reported using color bandpass filters. Higher levels of multiplexing have been reported with flow cytometry and multispectral imaging (Stack et al. (2014) Methods 70(1):46-58; Perfetto et al. (2004) 4(8):648-655).

Unfortunately, FL probes have not demonstrated the same level of sensitivity as CL and typically have a lower dynamic range. A reason for lower sensitivity with FL probes is the presence of background from autofluorescence of co-localized material or interference of fluorescence from other probes. A different technique was developed to reduce background from autofluorescence using longer lifetime fluorescent probes called time-resolved fluorescence (TRF) (Zuchner et al. (2009) Anal. Chem. 81(22):9449-9453; Kemper et al. (2001) Electrophoresis. 22(5):881-889; Lim et al. (1997) Anal Biochem. 245(2):184-195; Huhtinen et al. (2005) Anal. Chem. 77(8):2643-2648; Vereb et al. (1998) Biophys J. 74(5):2210-2222). In brief, autofluorescence typically has a relatively short lifetime (<20 ns) so that TRF detection is delayed in time until after the autofluorescence signal has died away. This is technically time gated detection, but has commonly been called time-resolved (Lakowicz, "Principles of Fluorescence Spectroscopy," 3rd Edition, Springer-Verlag, New York, 2006). The benefits of TRF detection have been well documented and include higher sensitivity, lower background, and wider dynamic range (Eliseeva & Bunzli (2010) Chem. Soc. Rev. 39(1):189-227; Bunzli & Piguet (2005) Chem. Soc. Rev. 34(12):1048-1077; Diamandis (1991) Clin. Chem. 37(9):1486-1491).

Multiplexing of TRF has been reported with some success. The use of Eu and Tb based probes has been demonstrated in biochemical assays using Time-Resolved Fluorescence Resonance Energy Transfer (TR-FRET) to detect two different proteins (Degorce et al. (2009) Curr. Chem. Genomics. 3:22-32; Bookout et al. (2000) J. Agric. Food Chem. 48(12):5868-5873; Hamy et al. (2001) J. Biomol. Screen. 6(3):179-187). In addition, there have also been reports of multiplexing with Eu and Sm, and Eu, Tb, and Sm (Bador et al. (1987) Clin. Chem. 33(1):48-51; Heinonen et al. (1997) Clin. Chem. 43(7):1142-1150). However, these systems suffer from cross talk as emission from one of the lanthanides bleeds into the detection channels of the other lanthanides. This limits the utility of these methods to having only one truly sensitive channel, while the other is limited by background signal from the second species.

Therefore, there is a need for an improved multiplexed system that maintains the high sensitivity, background rejection, stability, resistance to photo bleaching, and dynamic range of time-resolved fluorescence detection with minimal or no cross talk between channels.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a method for performing multiplexed time-resolved fluorescence (TRF) detection is provided comprising the following steps. First, a sample is provided comprising a first fluorescent label bound to a first analyte and a second fluorescent label bound to a second analyte, wherein the first fluorescent label has a first fluorescence emission lifetime which is at least 3 times longer than background fluorescence emission lifetimes, a first excitation wavelength, and a first emission wavelength, and the second fluorescent label has a second fluorescence emission lifetime, a second excitation wavelength, and a second emission wavelength; wherein the second fluorescence emission lifetime is at least 5 times longer than the first fluorescence emission lifetime. Next, the first fluorescent label is excited with a first excitation light having the first excitation wavelength, whereby the first fluorescent label emits a first detection signal having the first emission wavelength. Then, the second fluorescent label is excited with a second excitation light having the second excitation wavelength, whereby the second fluorescent label emits a second detection signal having the second emission wavelength. Next, intensity of the first detection signal is measured, wherein the intensity of the first detection signal is positively correlated with the amount of the first analyte in the sample. Then, intensity of the second detection signal is measured, wherein the intensity of the second detection signal is positively correlated with the amount of the second analyte in the sample.

In particular embodiments, the second fluorescence emission lifetime is at least 100 times or at least 1,000 times longer than the first fluorescence emission lifetime.

In other particular embodiments, the method for performing multiplexed TRF detection comprises the use of a second fluorescent label having a second fluorescence emission lifetime in a range of 100 μs to 1 ms, more particularly wherein the second fluorescent label is selected from the group consisting of lanthanide chelates of samarium (Sm(III)), dysprosium (Dy(III)), europium (Eu(III)), and terbium (Tb(III)). In further particular embodiments, the method for performing multiplexed TRF detection comprises the use of a first fluorescent label having a first fluorescence emission lifetime in a range of 0.1 μs to 10 μs, more particularly wherein the first fluorescent label is selected from the group consisting of transition metal chelates of ruthenium (Ru(II)), osmium (Os(II)), and rhenium (Re(I)).

In further particular embodiments, the fluorescent labels within the method for performing multiplexed TRF detection have a Stokes shift of greater than about 50 nanometers, in some embodiments greater than about 100 nanometers, and in some embodiments from about 250 to about 350 nanometers.

In other particular embodiments, the first analyte and the second analyte within the method for performing multiplexed TRF detection comprise proteins, more particularly membrane-bound proteins.

In other particular embodiments, the sample further comprises at least one additional fluorescent label bound to an additional analyte, wherein the additional fluorescent label has a label-specific excitation wavelength, a label-specific emission wavelength, and a label-specific fluorescence emission lifetime which is at least 3 times longer than background emission lifetimes; wherein the first fluorescence emission lifetime, the second fluorescence emission lifetime, and the label-specific fluorescence emission lifetime are each at least an order of magnitude different from one another. The additional fluorescent label is excited with a label-specific excitation light having the label-specific excitation wavelength, whereby the additional fluorescent label emits a label-specific detection signal having the label-specific emission wavelength. The intensity of the label-specific detection signal is then measured, wherein the intensity of the label-specific detection signal is positively correlated with the amount of the additional analyte in the sample. The at least one additional fluorescent label bound to an additional analyte may also comprise a plurality of different fluorescent labels bound to different analytes.

In a further embodiment, within the method for performing multiplexed TRF detection, the first analyte is a reference protein and the second analyte is an unknown protein, further wherein the second detection signal is normalized to the first detection signal.

In another embodiment, within the method for performing multiplexed TRF detection, the first analyte is a protein and the second analyte is a modified version of the protein, further wherein the ratio of modified protein to unmodified protein is calculated, particularly wherein the modified version of the protein is a phosphorylated version of the protein.

According to another embodiment, a multiplexed TRF detection system is configured for performing all or part of any of the methods disclosed herein.

According to another embodiment, a system for performing multiplexed TRF detection includes: a processor and a memory configured for performing all or part of any of the methods disclosed herein.

According to another embodiment, a computer-readable storage medium includes instructions for performing all or part of any of the methods disclosed herein.

According to another embodiment, a system includes the computer-readable storage medium.

According to another embodiment, a multiplexed time-resolved fluorescence (TRF) detection apparatus includes: a sample support configured for supporting a sample, the sample comprising a first fluorescent label and a second fluorescent label, wherein the first fluorescent label has a first fluorescence emission lifetime which is at least 3 times longer than background fluorescence emission lifetimes, a first excitation wavelength, and a first emission wavelength, and the second fluorescent label has a second fluorescence emission lifetime, a second excitation wavelength, and a second emission wavelength, and wherein the second fluorescence emission lifetime is at least 5 times longer than the first fluorescence emission lifetime; a light source configured for generating a first excitation light at the first excitation wavelength and a second excitation light at the second excitation wavelength; a light detector configured for measuring a first detection signal emitted from the sample in response to excitation by the first excitation light and a second detection signal emitted from the sample in response to excitation by the second excitation light; a computing device configured for: controlling the light source to generate the first excitation light and the second excitation light according to a timing sequence; and receiving an electrical output from the light detector corresponding to measurements of the first detection signal and the second detection signal.

According to another embodiment, the TRF detection apparatus includes an apparatus housing in which the light source and the light detector are positioned.

According to another embodiment, the TRF detection apparatus includes a cartridge removably installable in the apparatus housing. The cartridge may include one or more of the following components: the light source; the light detector; an excitation light optical system configured for directing the first excitation light and the second excitation light to the sample; and/or an emission light optical system configured for directing the first detection signal and the second detection signal to the light detector.

Other devices, apparatuses, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

FIGS. 3B through 3G are schematic views of components of the apparatus illustrated in FIG. 3A, in which various components of the apparatus are illustrated as contained inside or outside of cartridges according to some embodiments.

DETAILED DESCRIPTION

Figure 1:
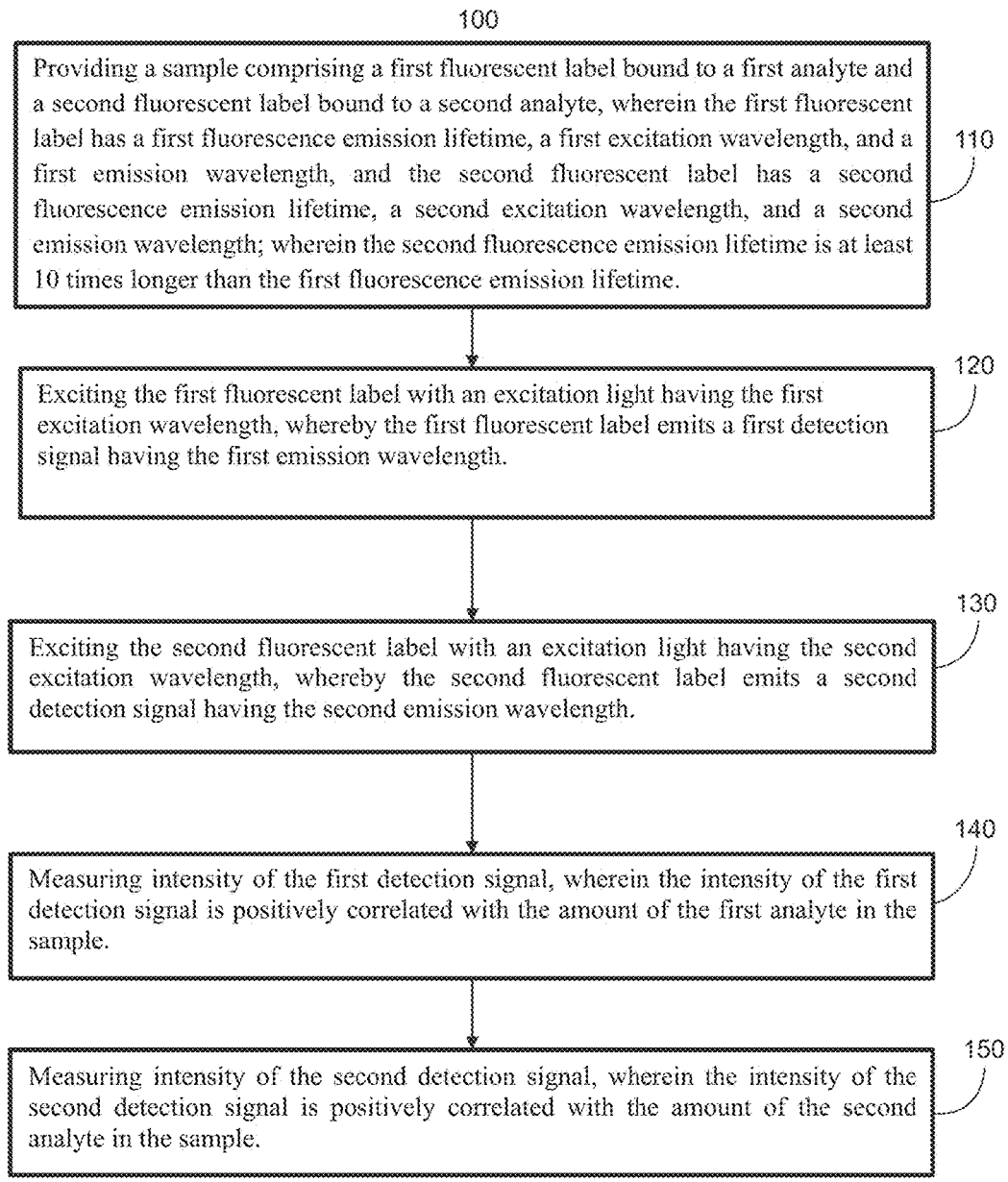
FIG. 1 is a flow chart of a method for multiplexed time-resolved fluorescence (TRF) detection according to some embodiments.

The present invention is directed to a novel method to multiplex long lifetime fluorescent dyes using TRF detection. A combination of spectral and temporal differences in fluorescence emission is used to enhance the ability to separate signals in an assay from multiple dyes. Multiplexed TRF detection apparatuses and systems configured for performing all or part of any of the methods disclosed herein are also provided, particularly apparatuses and systems incorporating cartridge-based multi-mode readers.

Conventional TRF detection involves exciting a fluorescent label with a short pulse of light, then typically waiting a certain time after excitation before measuring the remaining long-lived fluorescent signal. In this manner, any short-lived fluorescent background signals and scattered excitation radiation are eliminated. This ability to eliminate much of the background signals can result in sensitivities that are 2 to 4 orders greater than conventional fluorescence. Thus, TRF detection is designed to reduce background signals from the emission source or from scattering processes (resulting from scattering of the excitation radiation) by taking advantage of the fluorescence characteristics of certain fluorescent materials.

The typical selection criteria of fluorescent labels for TRF include a relatively long emission lifetime. As indicated above, this is desired so that the label emits its signal well after any short-lived background signals dissipate. A long fluorescence lifetime also makes it possible to use flashlamp excitation and low-cost circuitry for time-gated fluorescence measurements. In addition, the fluorescent label may have a relatively large "Stokes shift." The term "Stokes shift" is generally defined as the displacement of spectral lines or bands of luminescent radiation to a longer emission wavelength than the excitation lines or bands. A relatively large Stokes shift allows the excitation wavelength of the fluorescent label to remain far apart from its emission wavelengths and is desirable because a large difference between excitation and emission wavelengths makes it easier to eliminate excitation radiation from the emitted signal. Further, a large Stokes shift also minimizes interference from fluorescent molecules in the sample and/or light scattering due to proteins or colloids, which are present with some body fluids (e.g., blood). In addition, a large Stokes shift also minimizes the requirement for expensive, high-precision filters to eliminate background interference.

One type of fluorescent compound that has both a relatively long emission lifetime and relatively large Stokes shift are lanthanide chelates such as chelates of samarium (Sm(III)), dysprosium (Dy(III)), europium (Eu(III)), and terbium (Tb(III)). Such chelates can exhibit strongly red-shifted, narrow-band, long-lived emission after excitation of the chelate at substantially shorter wavelengths. Typically, the chelate possesses a strong ultraviolet excitation band due to a chromophore located close to the lanthanide in the molecule. Subsequent to excitation by the chromophore, the excitation energy can be transferred from the excited chromophore to the lanthanide. This is followed by a fluorescence emission characteristic of the lanthanide. Lanthanide chelates, for instance, have exceptionally large Stokes shifts of about 250 to about 350 nanometers, as compared to only about 28 nanometers for fluorescein. Also, the fluorescence of lanthanide chelates is long-lived, with lifetimes of about 100 to about 1000 microseconds, as compared to about 1 to about 20 nanoseconds for other fluorescent labels. In addition, these chelates have a very narrow emission spectra, typically having bandwidths less than about 10 nanometers at about 50% emission.

Another type of fluorescent compound that has both a relatively long emission lifetime and relatively large Stokes shift are transition metal chelates such as chelates of ruthenium (Ru(II)), osmium (Os(II)), and rhenium (Re(I)). The fluorescence lifetime of transition metal chelates is typically about 0.1 to about 10 microseconds.

As described above, the present invention is directed to a novel method to multiplex long lifetime fluorescent dyes using TRF detection. A combination of spectral and temporal differences in fluorescence emission is used to enhance the ability to separate signals in an assay from multiple dyes. The method exploits both time-domain and wavelength-domain differences between TRF dyes to reduce cross talk to below 1%, and more particularly to below 0.01%.

The multiplexed TRF detection methods of the present invention provide a number of advantages compared to conventional methods. For example, improved quantitation may be achieved by using one channel as a reference or standard. Using conventional methods for loading samples into a column on a gel to perform a Western Blot there can be significant error in how much sample actually makes it down the lane. By utilizing a reference protein (also known as a housekeeping protein) signal in one channel, then the signal from an "unknown" protein in a second (or third) channel can be normalized to the reference channel to improve relative accuracy.

Another advantage of the multiplexed TRF detection methods of the present invention is that they allow for improved ratiometric measurements. A common application of Western Blot is to look at phosphorylation of a protein as an indicator of a signaling event and calculate the ratio of phosphoprotein to unmodified (or total) protein. Using single channel Western Blot to calculate such a ratio requires measuring the first, stripping the Western Blot membrane, and then re-probing and measuring the second protein. Two-channel detection allows for probing and measurement of both phospho- and total-protein at the same time. This saves significant time and increases accuracy since sources of experimental error are removed by not having to strip and re-probe.

FIG. 1 is a flow chart of a method 100 for multiplexed TRF detection according to some embodiments. First, a sample is provided comprising a first fluorescent label bound to a first analyte and a second fluorescent label bound to a second analyte, wherein the first fluorescent label has a first fluorescence emission lifetime which is at least 3 times longer than background fluorescence emission lifetimes, a first excitation wavelength, and a first emission wavelength, and the second fluorescent label has a second fluorescence emission lifetime, a second excitation wavelength, and a second emission wavelength; wherein the second fluorescence emission lifetime is at least 5 times longer than the first fluorescence emission lifetime (step 110). Next, the first fluorescent label is excited with a first excitation light having the first excitation wavelength, whereby the first fluorescent label emits a first detection signal having the first emission wavelength (step 120). Then, the second fluorescent label is excited with a second excitation light having the second excitation wavelength, whereby the second fluorescent label emits a second detection signal having the second emission wavelength (step 130). Next, intensity of the first detection signal is measured, wherein the intensity of the first detection signal is positively correlated with the amount of the first analyte in the sample (step 140). Then, intensity of the second detection signal is measured, wherein the intensity of the second detection signal is positively correlated with the amount of the second analyte in the sample (step 150). In particular embodiments, the second fluorescence emission lifetime is at least 100 times or at least 1,000 times longer than the first fluorescence emission lifetime.

In other particular embodiments, the method for performing multiplexed TRF detection comprises the use of a second fluorescent label having a second fluorescence emission lifetime in a range of 100 μs to 1 ms, more particularly wherein the second fluorescent label is selected from the group consisting of lanthanide chelates of samarium (Sm (III)), dysprosium (Dy(III)), europium (Eu(III)), and terbium (Tb(III)). In further particular embodiments, the method for performing multiplexed TRF detection comprises the use of a first fluorescent label having a first fluorescence emission lifetime in a range of 0.1 μs to 10 μs, more particularly wherein the first fluorescent label is selected from the group consisting of transition metal chelates of ruthenium (Ru(II)), osmium (Os(II)), and rhenium (Re(I)).

In further particular embodiments, the fluorescent labels within the method for performing multiplexed TRF detection have a Stokes shift of greater than about 20 nanometers, in some embodiments greater than about 100 nanometers, and in some embodiments from about 250 to about 350 nanometers.

In further embodiments, prior to step 110 the sample is prepared according to the following steps:
  a) contacting the sample with:
    i) a first antibody that specifically binds the first analyte;
    ii) a second antibody that specifically binds the second analyte;
    iii) a first fluorescent antibody conjugate that specifically binds the first antibody, wherein the first fluorescent antibody conjugate comprises a first fluorescent label having a first fluorescence emission lifetime, a first excitation wavelength, and a first emission wavelength;
    iv) a second fluorescent antibody conjugate that specifically binds the second antibody, wherein the second fluorescent antibody conjugate comprises a second fluorescent label having a second fluorescence emission lifetime, a second excitation wavelength, and a second emission wavelength; and
  b) incubating the sample under conditions and for a time sufficient to allow the antibodies and the antibody conjugates to form immunocomplexes. In some embodiments, the antibodies and antibody conjugates may be provided in the form of a mixture in solution, or the antibodies and/or antibody conjugates may be attached to the surface of a solid support. The solid support may be, but is not limited to, magnetic beads, gold nanoparticles, biodegradable organic polymer nanoparticles, microwells, or microtiter plates. In other embodiments, the first or second antibodies may have the first or second fluorescent labels directly attached to them eliminating the need for antibody conjugates. Accordingly, the presently disclosed methods encompass a wide range of assays for the detection of analytes, such as the detection of proteins bound to membranes, proteins bound to beads, proteins in microfluidic channels (potentially separated), and/or proteins in gels or other viscous media (potentially separated).

In other particular embodiments, the sample within the method for performing multiplexed TRF detection comprises at least one additional fluorescent label bound to an additional analyte. The additional fluorescent label has a label-specific excitation wavelength, a label-specific emission wavelength, and a label-specific fluorescence emission lifetime which is at least 3 times longer than background emission lifetimes. Furthermore, the first fluorescence emission lifetime, the second fluorescence emission lifetime, and the label-specific fluorescence emission lifetime are each at least an order of magnitude different from one another. The additional fluorescent label is excited with a label-specific excitation light having the label-specific excitation wavelength, whereby the additional fluorescent label emits a label-specific detection signal having the label-specific emission wavelength. Intensity of the label-specific detection signal is then measured, wherein the intensity of the label-specific detection signal is positively correlated with the amount of the additional analyte in the sample. The at least one additional fluorescent label bound to an additional analyte may also comprise a plurality of different fluorescent labels bound to different analytes, wherein the at least one additional fluorescent label bound to an additional analyte comprises a plurality of different fluorescent labels bound to different analytes.

In a further embodiment, within the method for performing multiplexed TRF detection, the first analyte is a reference protein and the second analyte is an unknown protein, further wherein the second detection signal is normalized to the first detection signal.

In another embodiment, within the method for performing multiplexed TRF detection, the first analyte is a protein and the second analyte is a modified version of the protein, further wherein the ratio of modified protein to unmodified protein is calculated, particularly wherein the modified version of the protein is a phosphorylated version of the protein.

As used herein, the term "analyte" generally refers to a substance to be detected. For example, in other particular embodiments, the first analyte and the second analyte within the method for performing multiplexed TRF detection comprise proteins, more particularly membrane-bound proteins. Analytes may also include antigenic substances, haptens, antibodies, and combinations thereof. Accordingly, analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), drug intermediaries or byproducts, bacteria, virus particles and metabolites of or antibodies to any of the above substances.

As used herein, the term "sample" generally refers to a material known or suspected of containing the analyte. The sample may be used directly as obtained from the source or following a pretreatment to modify the character of the sample. The sample may be derived from any biological source, such as a physiological fluid, including, blood, interstitial fluid, saliva, ocular lens fluid, cerebral spinal fluid, sweat, urine, milk, ascites fluid, raucous, synovial fluid, peritoneal fluid, vaginal fluid, amniotic fluid or the like. The sample may be pretreated prior to use, such as preparing plasma from blood, diluting viscous fluids, and the like. Methods of pretreatment can involve filtration, precipitation, dilution, distillation, concentration, inactivation of interfering components, chromatography, separation steps, and the addition of reagents. Besides physiological fluids, other liquid samples may be used such as water, food products and the like for the performance of environmental or food production assays. In addition, a solid material known or suspected of containing the analyte may be used as the sample. In some instances it may be beneficial to modify a solid sample to form a liquid medium or to release the analyte.

The method 100 for multiplexed TRF detection described above may be implemented with the use of a suitable sample analyzing apparatus. In some embodiments, the flow chart of FIG. 1 may be considered as schematically representing a sample analyzing apparatus configured for carrying out all or part of the steps of the method 100 described above. Other examples of suitable sample analyzing apparatuses are described below with reference to FIGS. 2 to 3G.

Figure 2:
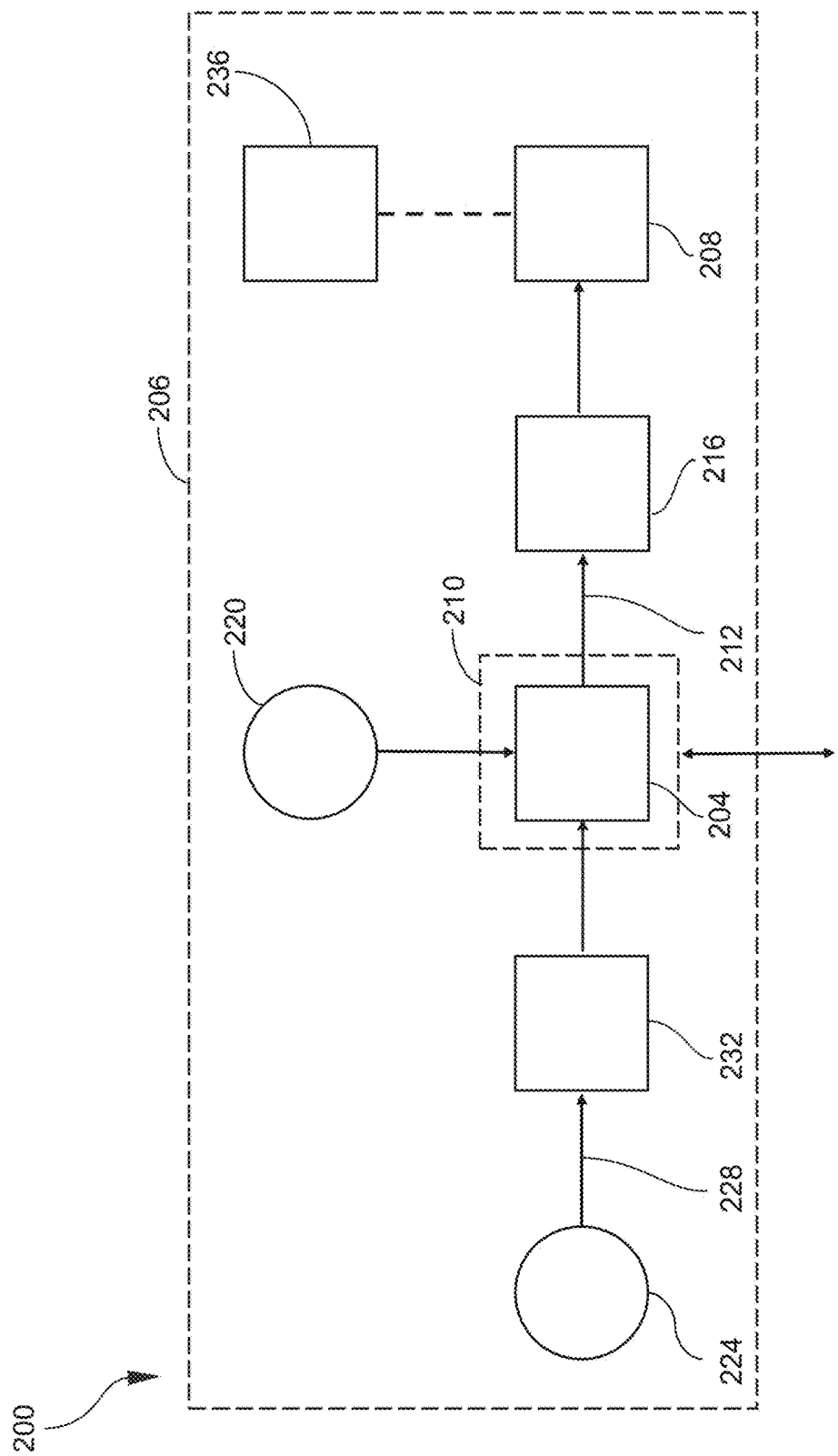
FIG. 2 is a schematic view of an example of a sample analyzing apparatus according to some embodiments.

FIG. 2 is a schematic view of an example of a sample analyzing according to some embodiments. The sample analyzing apparatus 200 is configured for performing multiplexed TRF detection on a sample to detect multiple analytes, as these terms have been defined elsewhere herein. In some embodiments, the sample analyzing apparatus 200 is configured to enable a user to select a desired type of optical measurement to be performed, not only TRF measurement but other fluorescence-based measurements as well as other types of optical measurements such as, for example, luminescence, absorbance, cell imaging, etc. For example, the user may be able to reconfigure the optics of the sample analyzing apparatus 200 to perform a desired type of fluorescence measurement. Thus, in some embodiments the sample analyzing apparatus 200 may be a multi-mode reader. For example, as a multi-mode reader the sample analyzing apparatus 200 may be reconfigurable by enabling a user to select an application-specific cartridge among a number of different cartridges available, and load the selected cartridge into the sample analyzing apparatus 200 so as to establish optical and electrical circuits specific to the desired application. The selected cartridge is coupled to the sample analyzing apparatus 200 whereby the sample analyzing apparatus 200 is properly configured for carrying out the selected experiment. The cartridge may contain optics specific to or optimized for a particular type of application such as, for example, multiplexed TRF detection. The internal optics housed within the cartridge may communicate with external optics housed within the housing of the sample analyzing apparatus 200 through optical ports of the cartridge's housing. Some cartridges may additionally include one or more internal light sources and/or one or more light detectors. Examples of cartridge-based multi-mode readers are described in U.S. Patent Application Pub. No. 2014/0191138 and U.S. Pat. No. 8,119,066, the entire contents of which are incorporated by reference herein in their entireties.

Generally, the structure and operation of the various components provided in optical-based sample analysis instruments are understood by persons skilled in the art, and thus are only briefly described herein to facilitate an understanding of the presently disclosed subject matter. In the illustrated embodiment, the sample analyzing apparatus 200 includes a sample support 204 configured for supporting one or more samples under analysis, and a light detector 208 configured for receiving and measuring emitted light 212 emitted from the sample. The sample support 204 when in an operative position for carrying out optical measurement of the sample, and the light detector 208 and other components illustrated in FIG. 2, may be enclosed in an apparatus housing 206 of the sample analyzing apparatus 200. The apparatus housing 206 may include one or more panels, doors, drawers, etc. for loading the sample support 204 and cartridges if provided, accessing interior regions of the sample analyzing apparatus 200, etc.

Generally, the sample support 204 may be one or more containers configured for holding one or more samples during an analysis. As non-limiting examples, the sample support 204 may be a multi-well plate (also known as a microtiter plate, microplate, or optical plate), one or more cuvettes, etc. The sample support 204 may be disposed on a sample carrier (or sample support carrier) 210 configured for moving the sample support 204 along more or more axes. For example, the sample carrier 210 may be a manually actuated, semi-automated, or motorized stage or platform. The sample carrier 210 may be movable into and out from the apparatus housing 206, as indicated by an arrow in FIG. 2. A sample, or the sample support 204 containing one or more samples, may be mounted onto the sample carrier 210 while the sample carrier 210 is at an outside position, e.g., where the sample carrier 210 is positioned at least partially outside the apparatus housing 206. The sample carrier 210 may thus also be considered as a sample support. The sample carrier 210 may then be moved to an inside position at which the sample carrier 210 is positioned entirely in the apparatus housing 206 so as to align the sample (or successively align multiple samples) with an optical component and/or liquid handling component of the sample analyzing apparatus 200

In various embodiments, the optical input end of the light detector 208 typically includes a lens. The output end may include an electrical connector (e.g., contacts, terminals, pins, wire support, etc.) to provide power and enable measurement signals generated by the light detector 208 to be outputted to signal processing circuitry (e.g., data acquisition circuitry) provided with or external to the sample analyzing apparatus 200. Depending on the embodiment, the light detector 208 may be a photomultiplier tube (PMT), a photodiode, a charge-coupled device (CCD), an active-pixel sensor (APS) such as a complementary metal-oxide-semiconductor (CMOS) device, etc., as needed to optimize sensitivity to the emission wavelengths to be detected.

In typical embodiments, the sample analyzing apparatus 200 further includes emission optics 216 configured for transmitting the emitted light 212 from the sample to the light detector 208. The emission optics 216 may also be configured for processing the emitted light 212. Examples of processing include, but are not limited to, collecting, focusing, collimating, filtering, beam steering, beam splitting, and optical path switching. Thus, depending on the embodiment, the emission optics 216 may include one or more lenses, read heads, apertures, filters, light guides, mirrors, beam splitters, monochromators, diffraction gratings, prisms, optical path switches, etc. The emission optics 216 may configured for receiving emitted light 212 from above the sample (e.g., a top read head) and/or below the sample (e.g., a bottom read head).

In some embodiments, the sample analyzing apparatus 200 further includes a liquid dispensing system 220 (e.g., injector needle, tubing, pump, etc.) configured for adding a liquid to the sample (e.g., into selected wells of the sample support 204) before or after the sample has been operatively positioned in the sample analyzing apparatus 200. For example, a labeling agent may be added to the sample for fluorescence, luminescence or other types of measurements, as appreciated by persons skilled in the art. In some embodiments, two or more different types of reagents may be added.

In embodiments requiring excitation such as the multiplexed TRF detection techniques disclosed herein, the sample analyzing apparatus 200 includes one or more light sources 224 for producing excitation light 228 of a desired wavelength that is directed to the sample. Depending on the embodiment, the light source 224 may include a broadband light source (e.g., flash lamp) or one or more light emitting diodes (LEDs), laser diodes (LDs), lasers, etc. Multiple light sources 224 may be provided to enable a user to select a desired excitation wavelength. In typical embodiments, the sample analyzing apparatus 200 further includes excitation optics 232 configured for transmitting the excitation light 228 from the light source 224 to the sample. The excitation optics 232 may include, for example, one or more lenses, read heads, apertures, filters, light guides, mirrors, beam splitters, monochromators, diffraction gratings, prisms, optical path switches, etc., as noted above.

In embodiments in which the light source is an LED light source, the sample analyzing apparatus 200 (or a cartridge operatively coupled to the sample analyzing apparatus 200) may have an electronic current supply that is capable of pulsing the LED light source, a control for changing the intensity of the exciting light from the LED light source, and/or a photodiode that is capable of measuring the intensity of exciting light produced by the light source, which may be used to stabilize the LED light source. Preferred LED light sources are obtained from Lumileds, San Jose, Calif.; Luxeon Star, Nichia, Tokushima, Japan; and Roithner-Laser, Vienna, Austria. In other embodiments, the light source may be a Xenon flash lamp module, the module having a Xenon flash lamp as the light source and having the corresponding electronics to produce a pulsed light source. In the case of using a wide band light source, such as a Xenon flash lamp, the optical system includes a wavelength selector, filter, or the like for controlling the wavelength of the exciting light. Preferred Xenon flash lamp modules are obtained from Excelitas, Waltham, Mass.; and Hamamatsu Photonics, Japan.

As also schematically illustrated in FIG. 2, the sample analyzing apparatus 200 may further include a computing device (or system controller) 236. As appreciated by persons skilled in the art, the computing device 236 may represent one or more modules configured for controlling, monitoring and/or timing various functional aspects of the sample analyzing apparatus 200, and/or for receiving data or other signals from the sample analyzing apparatus 200 such as measurement signals from the light detector 208 and control signals to the light detector 208. For all such purposes, the computing device 236 may communicate with various components of the sample analyzing apparatus 200 via wired or wireless communication links, as depicted by a dashed line between the computing device 236 and the light detector 208. For simplicity, other communication links that may be present between the computing device 236 and other components of the sample analyzing apparatus 200 are not shown. In typical embodiments, the computing device 236 includes a main electronic processor providing overall control, and may include one or more electronic processors configured for dedicated control operations or specific signal processing tasks. The computing device 236 may also include one or more memories and/or databases for storing data and/or software. The computing device 236 may also include a computer-readable medium 236 that includes instructions for performing any of the methods disclosed herein. The functional modules of the computing device 236 may comprise circuitry or other types of hardware (or firmware), software, or both. For example, the modules may include signal processing (or data acquisition) circuitry for receiving measurement signals from the light detector 208 and software for processing the measurement signals such as for generating graphical data. The computing device 236 may also be representative of one or more types of user interface devices, such as user input devices (e.g., keypad, touch screen, mouse, and the like), user output devices (e.g., display screen, printer, visual indicators or alerts, audible indicators or alerts, and the like), a graphical user interface (GUI) controlled by software, and devices for loading media readable by the electronic processor (e.g., logic instructions embodied in software, data, and the like). The computing device 236 may include an operating system (e.g., Microsoft Windows® software) for controlling and managing various functions of the computing device 236.

According to some embodiments, an experiment entailing optical measurement utilizing the analyzing apparatus 200 may be implemented as follows. The sample is introduced into the sample analyzing apparatus 200 and placed in a proper operating position relative to optics and other components of the sample analyzing apparatus 200. Generally, the "operating" position of the sample is an "optically aligned" position, i.e., a position that establishes an optical path sufficient for optical data acquisition from the sample. Depending on the experiment, the operating position may also correspond to the sample being "fluidly aligned" with the sample analyzing apparatus 200, i.e., positioned so as to be able to dispense fluid onto the sample such as by operating the liquid dispensing system 220. Sample introduction may entail loading one or more samples in one or more wells of a microplate or other type of sample support 204, and loading or mounting the sample support 204 in the sample analyzing apparatus 200, such as with the use of a sample carrier 210 as noted above. Also as noted above, depending on the sample and the type of measurement to be made, the sample may be subjected to preparation or treatment (incubation, mixing, homogenization, centrifuging, buffering, reagent addition, etc.) prior to being positioned in the sample analyzing apparatus 200, as appreciated by persons skilled in the art.

In addition to sample introduction, the sample analyzing apparatus 200 or certain components thereof (optics, electronics, etc.) may need to be configured for implementing the specific type of measurement to be made. For example, if cartridge-based, the appropriate cartridge (or cartridges) may be installed in the sample analyzing apparatus 200. After installing a cartridge, optics provided in the cartridge become part of the optical circuit within the housing 206 of the sample analyzing apparatus 200. For example, the cartridge optics may be aligned with (in optical communication with) the emission optics 216 and light detector 208, and in some embodiments also with the excitation optics 232 and light source 224. Installing the cartridge results in establishing electrical paths for transmitting power, data and control signals to and/or from the cartridge.

The sample is then processed as necessary to induce the emission of photons from the sample which, for fluorescence, entails the addition of reagents using the liquid dispensing system 220 and/or irradiation/excitation using the light source 224 and associated excitation optics 232. The emission optics 216 collect the emitted light 212 from the sample and direct the emitted light 212 to the light detector 208. The light detector 208 converts these optical signals into electrical signals (detector signals, or measurement signals) and transmits the electrical signals to signal processing circuitry, such as may be provided by a computing device 236 of the sample analyzing apparatus 200 as described above. In the case of multiple samples, the sample support 204 may be moved (such as by using a sample carrier 210 as described above) to sequentially align each additional sample with the optics being utilized for the experiment, whereby measurements are taken from all samples sequentially.

As noted above, the sample analyzing apparatus 200 may be utilized to carry out all or part of the method 100 for multiplexed TRF detection described above in conjunction with FIG. 1. Accordingly, the sample analyzing apparatus 200 may also be referred to as a multiplexed TRF detection apparatus. For example, the light source 224 may be operated to irradiate the sample with a first excitation signal having a first excitation wavelength optimized for exciting a first fluorescent label of the sample, and with a second excitation signal having a second excitation wavelength optimized for exciting a second fluorescent label of the sample. The light detector 208 may be operated to measure a first detection signal emitted from the sample at a first emission wavelength in response to excitation by the first excitation signal, and a second detection signal emitted from the sample at a second emission wavelength in response to excitation by the second excitation signal. For these purposes, in some embodiments the light source 224 may include at least two discrete light sources and/or the light detector 208 may include at least two discrete light detectors.

Figure 3A:
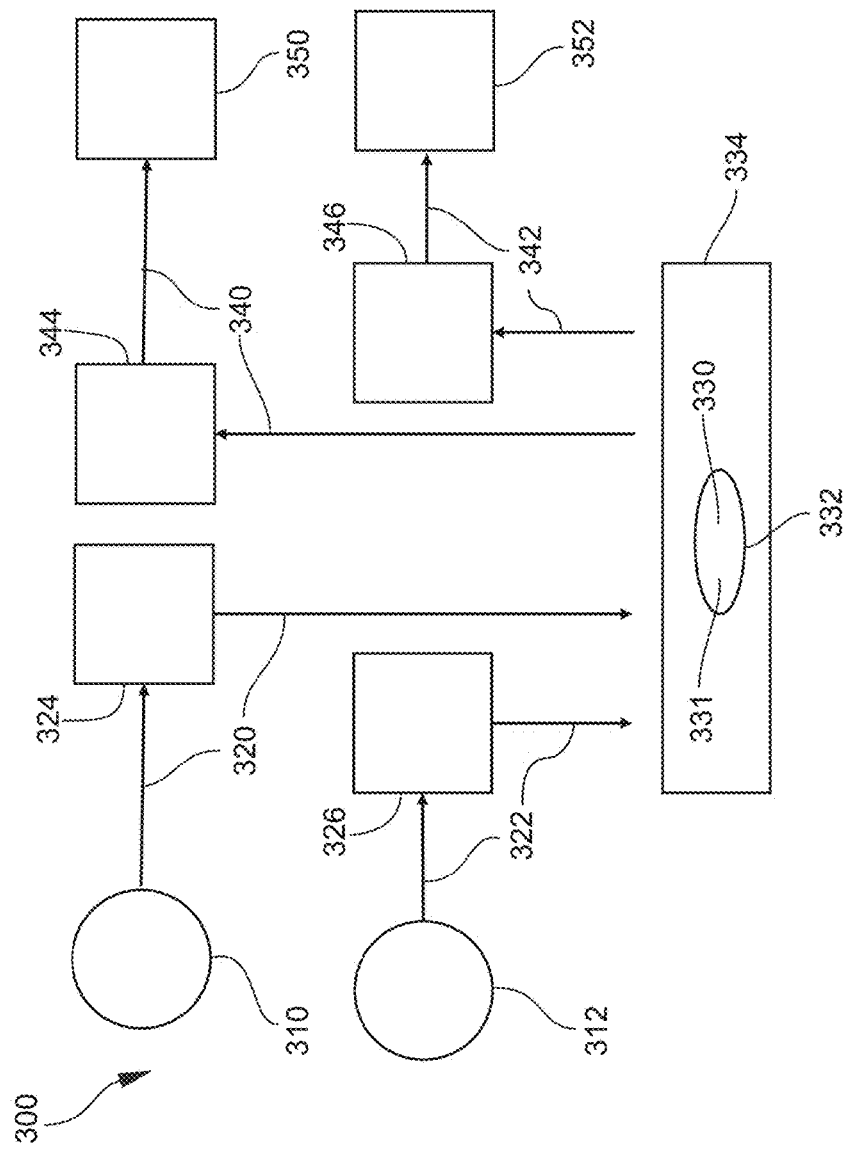
FIG. 3A is a schematic view of an example of an apparatus for multiplexed TRF detection according to some embodiments.

According to another embodiment, an apparatus for multiplexed TRF detection (or multiplexed TRF detection apparatus) is provided. Referring now to FIG. 3A, an apparatus 300 for multiplexed TRF detection is shown. A sample 332 may be held within the apparatus 300 on a sample support 334, such as a microplate. The apparatus 300 comprises a first light source 310 that produces a first excitation light 320 and a second light source 312 that produces a second excitation light 322. The apparatus 300 has a first excitation light optical system 324 and a second excitation light optical system 326, which have components for directing the first excitation light 320 and second excitation light 322, respectively, to the sample 332 as described above in conjunction with FIG. 2. The sample 332, containing a first analyte 330 and a second analyte 331, emits a first emitted light 340 and a second emitted light 342. The apparatus 300 has a first emitted light optical system 344 which receives the first emitted light 340 and a second emitted light optical system 346 which receives the second emitted light 342. The first emitted light optical system 344 then directs the first emitted light 340 to a first detector 350, and the second emitted light optical system 346 then directs the second emitted light 342 to a second detector 352. The foregoing components may be positioned in a main apparatus housing of the apparatus 300 (e.g., the apparatus housing 206 illustrated in FIG. 2).

FIGS. 3B through 3G are schematic views of components of the apparatus 300 illustrated in FIG. 3A, in which various components of the apparatus are illustrated as contained inside or outside of one or more cartridges according to some embodiments. Such cartridge(s) may be loaded or installed in the apparatus such that the cartridge(s) are enclosed in the interior of a main apparatus housing of the apparatus (e.g., the apparatus housing 206 illustrated in FIG. 2). Examples of cartridge-based readers are described in above-referenced U.S. Patent Application Pub. No. 2014/0191138 and U.S. Pat. No. 8,119,066.

Figure 3B:
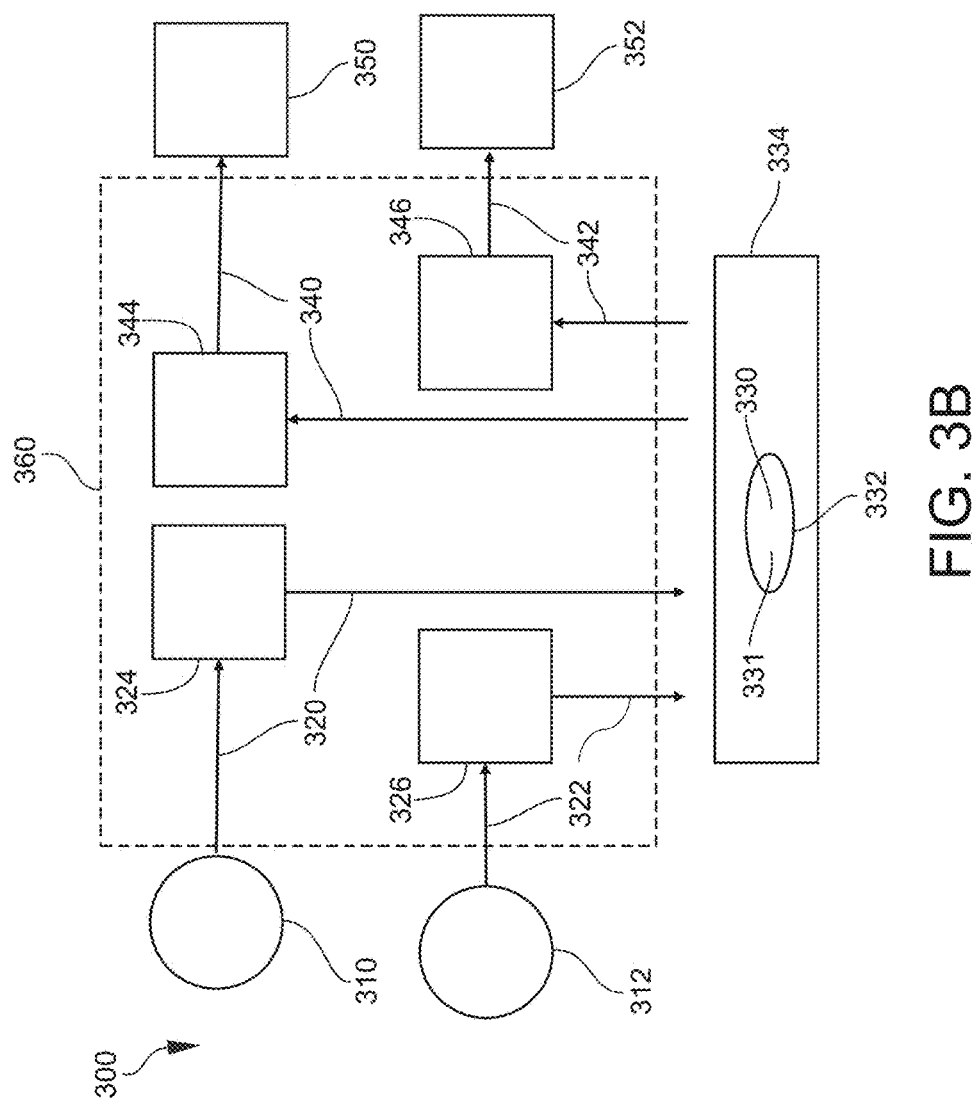

Referring now to FIG. 3B, the apparatus 300 further comprises a cartridge 360 comprising the first excitation light optical system 324, the second excitation light optical system 326, the first emitted light optical system 344, and the second emitted light optical system 346.

Referring now to FIG. 3C, the apparatus 300 further comprises a cartridge 360 comprising the first light source 310, the second light source 312, the first excitation light optical system 324, and the second excitation light optical system 326.

Figure 3D:
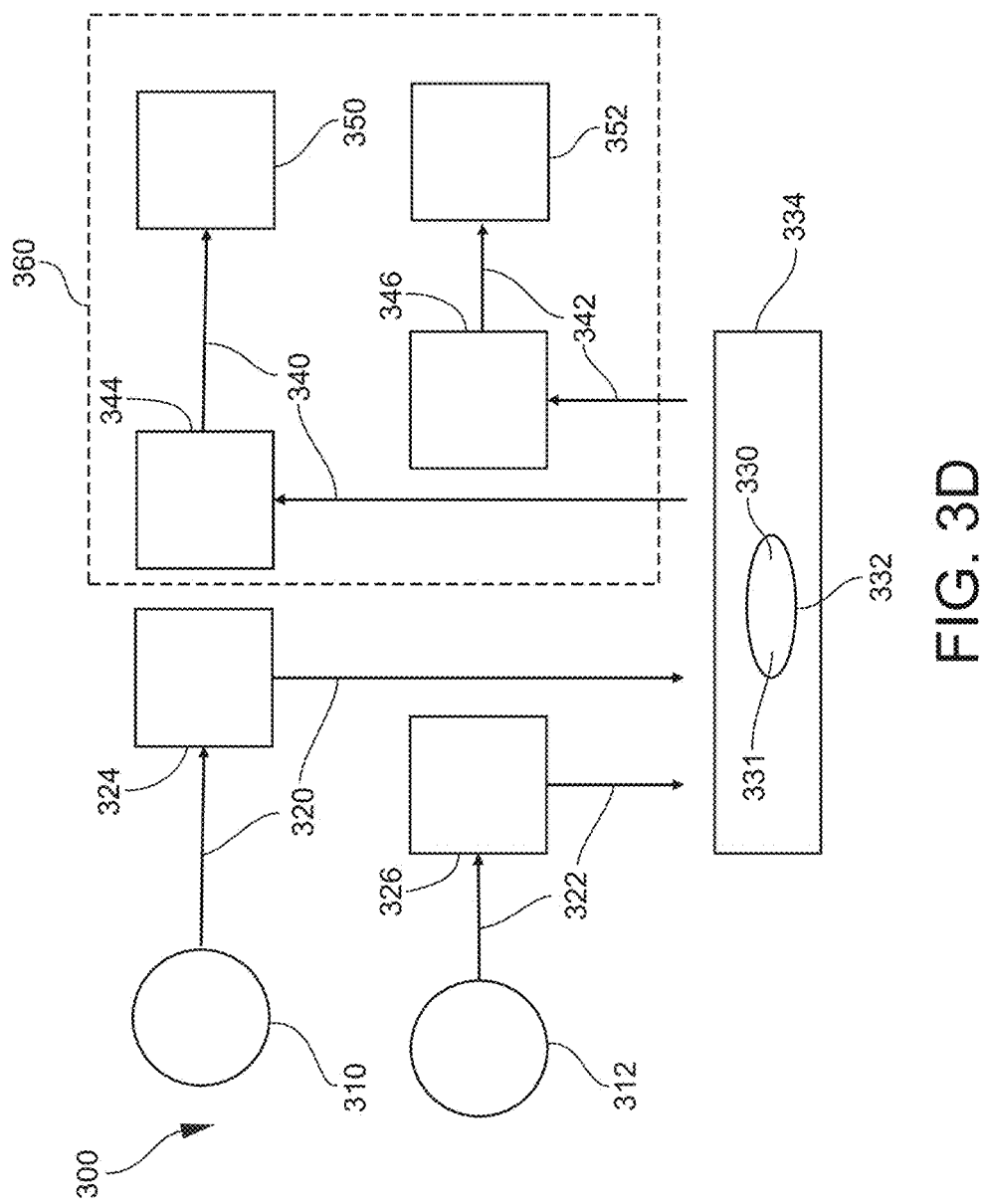

Referring now to FIG. 3D, the apparatus 300 further comprises a cartridge 360 comprising the first emitted light optical system 344, the second emitted light optical system 346, the first detector 350, and the second detector 352.

Figure 3E:
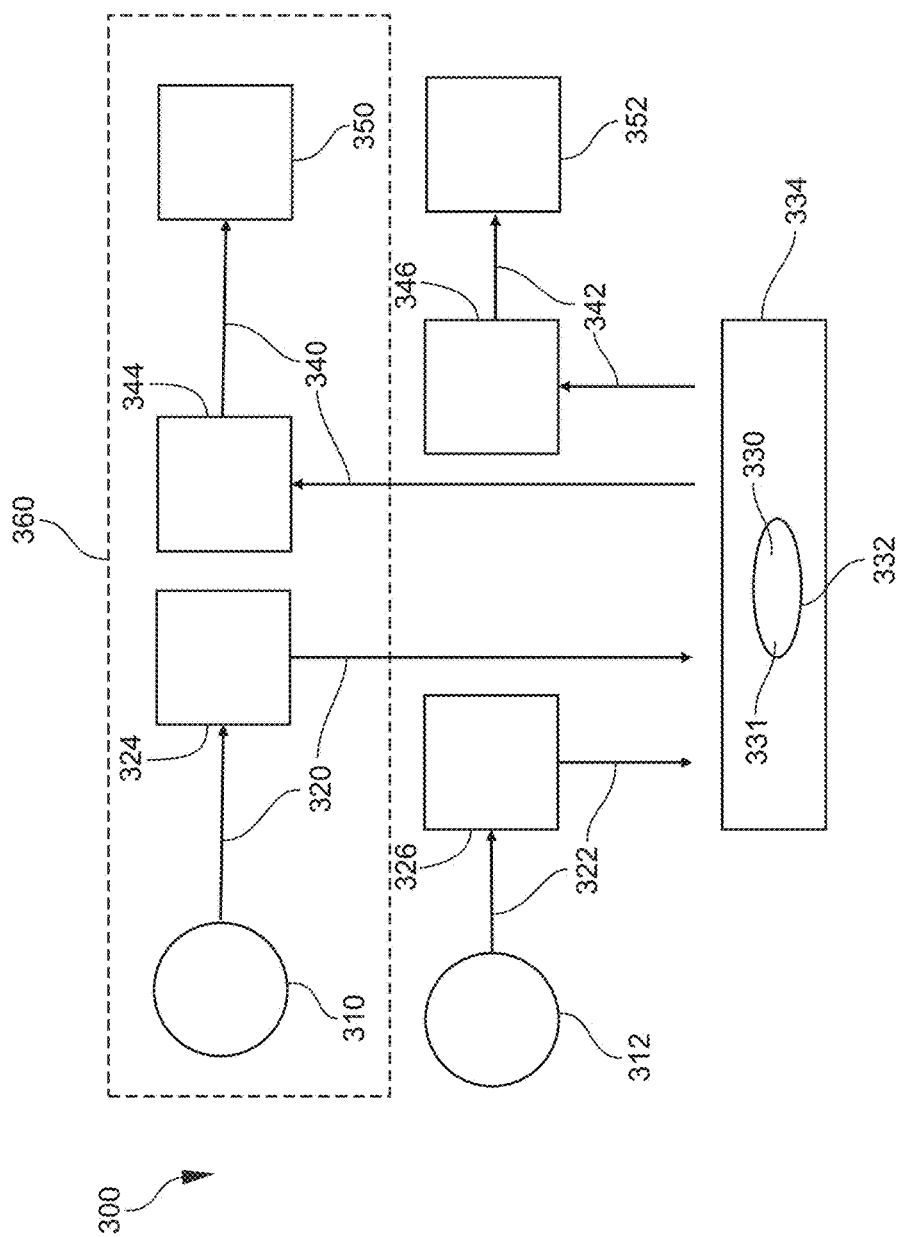

Referring now to FIG. 3E, the apparatus 300 further comprises a cartridge 360 comprising the first excitation light optical system 324, the first light source 310, the first emitted light optical system 344, and the first detector 350.

Figure 3F:
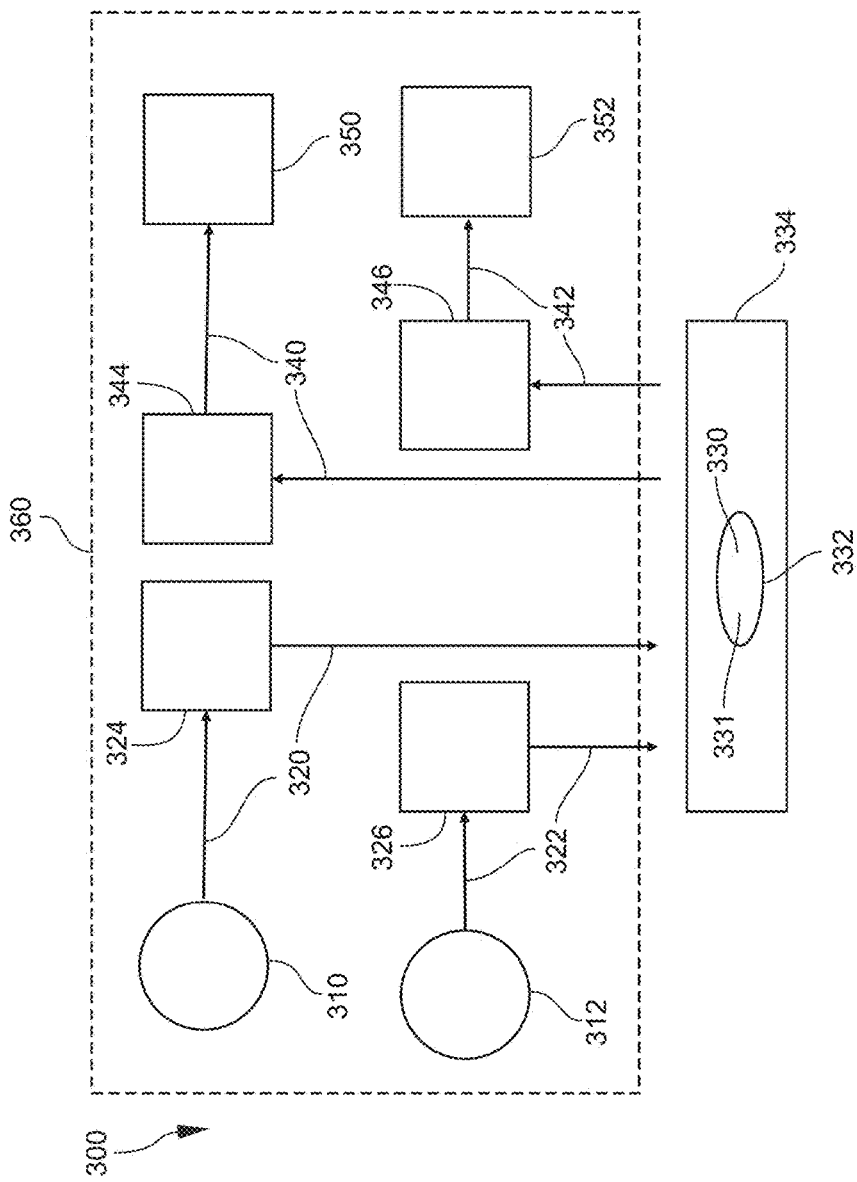

Referring now to FIG. 3F, the apparatus 300 further comprises a cartridge 360 comprising the first light source 310, the second light source 312, the first excitation light optical system 324, the second excitation light optical system 326, the first emitted light optical system 344, the second emitted light optical system 346, the first detector 350, and the second detector 352.

Referring now to FIG. 3G, the apparatus 300 further comprises a first cartridge 360 comprising the first light source 310, the first excitation light optical system 324, the first emitted light optical system 344, and the first light detector 350. The apparatus 300 further comprises a second cartridge 370 comprising the second light source 312, the second excitation light optical system 326, the second emitted light optical system 346, and the second light detector 352. In alternative embodiments, the first cartridge 360 may not contain both the first light source 310 and the first light detector 350 as shown, and in further embodiments both the first light source 310 and the first light detector 350 may be external to the first cartridge 360. Likewise, the second cartridge 370 may not contain both the second light source 312 and the second light detector 352 as shown, and in further embodiments both the second light source 312 and the second light detector 352 may be external to the second cartridge 370.

It will be understood to one of skill in the art that, for methods of multiplexed TRF detection involving at least one additional fluorescent label bound to an additional analyte, apparatuses and systems will be configured for performing excitation and detection of the additional fluorescent label. For example, an additional light source configured for generating the label-specific excitation light at the label-specific excitation wavelength could be used, as well as an additional light detector configured for measuring the label-specific detection signal emitted from the sample in response to excitation by the label-specific excitation light. Where the at least one additional fluorescent label bound to an additional analyte comprises a plurality of different fluorescent labels bound to different analytes, a plurality of different additional light sources and light detectors could be used.

Examples

Protein detection and characterization is an important task for pharmaceutical and clinical research. For example, protein detection and characterization can provide information on up and down regulation of proteins in cells, phosphorylation during cell signaling, and expression of transfected proteins. Multiple techniques have been developed for protein analysis including plate reader based enzyme-linked immunosorbant assays (ELISA), sodium dodecyl sulfate-polyacrylamide gel electrophoresis (SDS-PAGE), and spot or bead based capture systems that utilize luminescence read outs. However, improvement in analytical methods for the detection and quantitation of proteins is important to provide better tools to help understand disease mechanisms.

A number of luminescence probes have been developed to enable detection and analysis of proteins. Typically probes are attached to primary or secondary antibodies that then bind selectively to the protein of interest. These probes can be fluorescent molecules that produce light upon excitation with electromagnetic radiation or reactive species that will produce light when they are put in contact with another reactive molecule (e.g., a substrate) or some other stimulant (e.g., electrical current). Such probes are versatile as they can be attached through well-known chemical reactions to proteins, nucleotides, or small molecules. The relative amount of protein in a sample can be determined by the amount of light produced by the probes leading to the ability to do protein quantitation. Such probes also facilitate determining the spatial location of a protein of interest from low resolution (100-1000 μM) spots or blots to high resolution (<1 μM) sub-cellular imaging. These probes can be organic dyes, inorganic compounds, fluorescent proteins, or enzymes.

Chemiluminescence (CL) is a common method for detection of proteins in biochemical analyses or on surface-bound and spatially separated proteins. An example of the latter is the method of sodium dodecyl sulfate-polyacrylamide gel electrophoresis (SDS-PAGE) with electrophoretic transfer of proteins to a membrane, referred to as Western Blot (WB) analysis (Towbin et al. (1979) *Proc. Natl. Acad. Sci. U.S.A.* 76(9):4350-4354; Renart et al. (1979) *Proc. Natl. Acad. Sci. U.S.A.* 76(7):3116-3120). Electro-chemiluminescence (ECL) has also been applied to detect proteins bound to spots in specially designed multiwell plates (e.g., MULTI SPOT® and MULTI-ARRAY™ plates and SECTOR™ instruments, Meso Scale Discovery, a division of Meso Scale Diagnostics, LLC, Gaithersburg, Md.).

An advantage of CL and ECL is very high sensitivity with limits of detection for proteins in solution in the sub-picogram/ml range. However, these systems produce transient signals, are not stable, and require a complicated procedure to produce the chemical reaction required for detection. They are also non-linear systems (i.e., one probe produces many photons) and have poor reproducibility so are not suitable for applications where quantitation of protein amount is desired. A last, but significant limitation is the inability to multiplex multiple CL signals. Their emissions are very broad and that makes the ability to detect two different CL emissions from the same spatial location very challenging.

Fluorescence (FL) probes overcome some of the limitations of CL. They provide ability for better quantitation since the relationship between excitation photons and emission photons is, in general, linear. They are also more versatile as there is no need to provide access to the probes by other reactive molecules. In general, FL probes are also more stable, especially when protected from light as they are generally non-reactive chemical species. Perhaps the most important advantage of FL probes is that they provide the ability to perform multiplexing. FL molecules come in a wide variety of forms with a wide range of excitation and emission bands. Thus two (or more) probes at the same spatial location can be independently excited and detected with minimal overlap (or cross-talk) between detection channels. The ability to detect up to four independent fluorophores from the same spatial location is regularly reported using color bandpass filters. Higher levels of multiplexing have been reported with flow cytometry and multispectral imaging (Stack et al. (2014) *Methods* 70(1):46-58; Perfetto et al. (2004) 4(8):648-655).

Unfortunately, FL probes have not demonstrated the same level of sensitivity as CL and typically have a lower dynamic range. A reason for lower sensitivity with FL probes is the presence of background from autofluorescence of co-localized material or interference of fluorescence from other probes. A different technique was developed to reduce background from autofluorescence using longer lifetime fluorescent probes called time-resolved fluorescence (TRF) (Zuchner et al. (2009) *Anal. Chem.* 81(22):9449-9453; Kemper et al. (2001) *Electrophoresis.* 22(5):881-889; Lim et al. (1997) *Anal Biochem.* 245(2):184-195; Huhtinen et al. (2005) *Anal. Chem.* 77(8):2643-2648; Vereb et al. (1998) *Biophys J.* 74(5):2210-2222). In brief, autofluorescence typically has a relatively short lifetime (<20 ns) so that TRF detection is delayed in time until after the autofluorescence signal has died away. This is technically time gated detection, but has commonly been called time resolved (Lakowicz, "Principles of Fluorescence Spectroscopy," 3rd Edition, Springer-Verlag, New York, 2006). The benefits of TRF detection have been well documented and include higher sensitivity, lower background, and wider dynamic range (Eliseeva & Bunzli (2010) *Chem. Soc. Rev.* 39(1):189-227; Bunzli & Piguet (2005) *Chem. Soc. Rev.* 34(12):1048-1077; Diamandis (1991) *Clin. Chem.* 37(9):1486-1491).

Significant effort has been made to develop and optimize TRF probes based on lanthanide coordination complexes with the most popular entities based on Eu and Tb (Kemper et al. (1999) *J. Biomol. Screen.* 4(6):309-314; Lopez et al. (1993) *Clin. Chem.* 39(2):196-201; Degorce et al. (2009) *Curr. Chem. Genomics.* 3:22-32). These probes have a wide range of use besides membranes and have shown good sensitivity for detection of proteins in histologic sections and in living cells (Su et al. (2005) *Anal. Biochem.* 347(1):89-93; Gahlaut & Miller (2010) *Cytometry A.* December 2010; 77(12):1113-1125). Various instruments have been developed for measurement of TRF especially for 2-dimensional arrays. The lanthanide probes can be imaged using standard camera systems with ultraviolet (uv) excitation, although reported sensitivities are only in the nanogram of protein range (Kemper et al. (2001) *Electrophoresis.* 22(5):881-889). Improvements in sensitivity can be made by using time-gated cameras with chopped or pulsed high intensity uv light sources (Gahlaut & Miller (2010) *Cytometry A.* 77(12): 1113-1125). However, this increases the overall cost of the instrumentation. A spot scanning system was developed using a pulsed uv laser and time-gated photon counting (Zuchner et al. (2009) *Anal. Chem.* 81(22):9449-9453). Excellent sensitivity for both Dot Blots and Western Blots were reported as well as extended dynamic range compared to chemiluminescence and fluorescence.

Figure 4A:
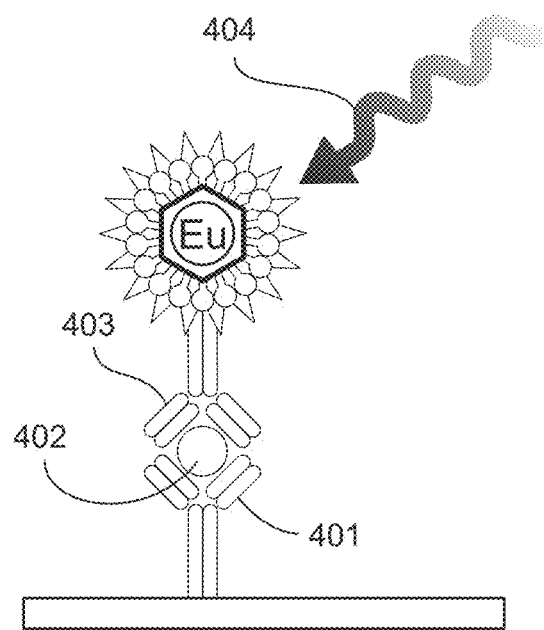
FIG. 4A is a schematic view of a method of TRF detection using a ScanLater™ Western Blot Detection System (Molecular Devices, LLC, Sunnyvale, Calif.).
Figure 4B:
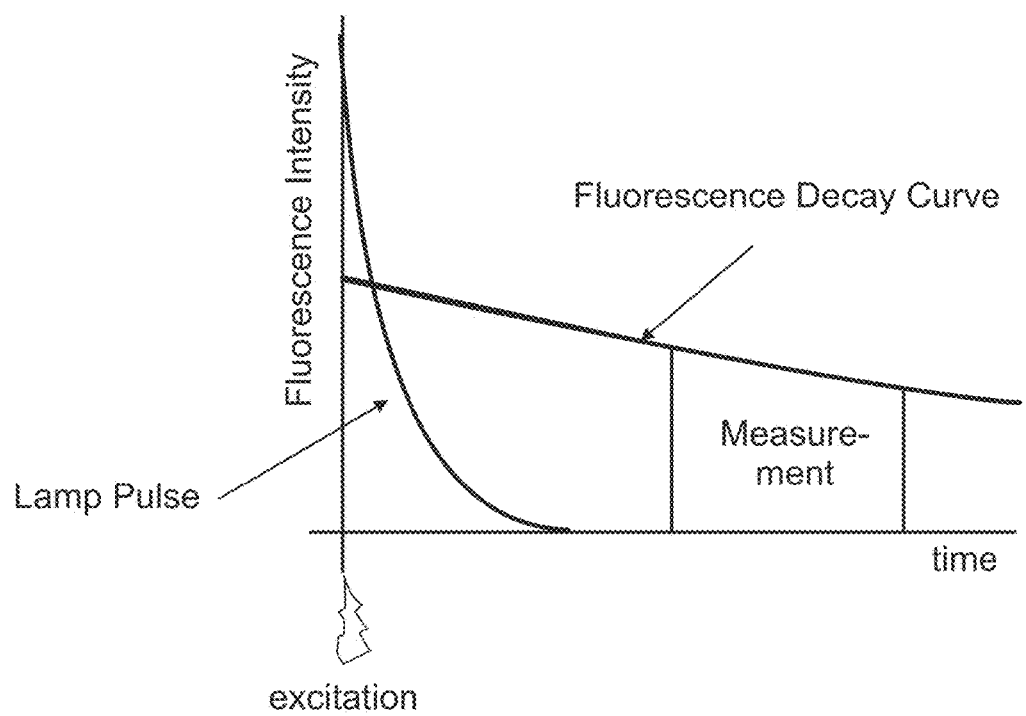
FIG. 4B is a schematic view illustrating principles of TRF detection.

We have demonstrated capability for detection and quantification of membrane bound proteins labeled with TRF stains. Membranes are incubated with Europium-chelate labeled secondary antibodies or streptavidin that bind specifically to the protein of interest. Europium (Eu) has a long fluorescence lifetime, on the order of 1 msec, and detection is done in time resolved fluorescence (TRF) mode with 50 μs delay which significantly reduces background from autofluorescence or other sources of short lifetime emissions (see FIGS. 4A and 4B). FIG. 4A is a schematic view of one non-limiting example of a method of TRF detection using the ScanLater™ Western Blot Detection System (Molecular Devices, LLC, Sunnyvale, Calif.), which in some embodiments may utilize a cartridge configured specifically for WB detection. An existing primary antibody 401 binds to a protein of interest 402. An Eu-labeled secondary antibody 403 then binds to the primary antibody 401. The ScanLater™ system is then utilized for detection (measurement) 404. It will be understood that a detection system other than the ScanLater™ system may be utilized. FIG. 4B is a schematic view illustrating principles of TRF detection. FIG. 4B plots intensity of the lamp excitation pulse and fluorescence decay as a function of time, with time=0 corresponding to the initiation of the excitation pulse. FIG. 4B also shows the period of time during which measurement may be taken relative to the preceding excitation pulse.

The membranes are placed into a plate reader system where they are scanned with a flash-lamp based TRF cartridge that has been optimized for WB scanning. The flash-lamp reduces the cost of the system as compared to the pulsed uv laser system previously reported while maintaining sensitivity (Zuchner et al. (2009), *Anal. Chem.* 81(22): 9449-9453). The method does not involve enzyme detection, and the Eu-chelates are resistant to photo-bleaching so the signal remains stable for long periods of time (weeks to months). This allows repeat reading of membranes and potential for comparison of band intensities to known standards for more accurate quantitation.

The TRF detection employs photon counting; hence the theoretical dynamic range is $>10^5$. In practice, dynamic range is limited by saturation of binding sites on high-abundance bands and non-specific binding to background membrane. There is also no camera "blooming" from saturation with high intensity light, as can occur with chemiluminescence or fluorescence detection, thus the system gives sharp bands and excellent image quality. This system provides a substrate-free environment for membrane-bound protein analysis with high sensitivity, broad dynamic range, and long-term stability. It provides advantages over current systems by allowing improved quantification and the ability to re-scan samples for reference or as instrument standards.

Figure 5A:
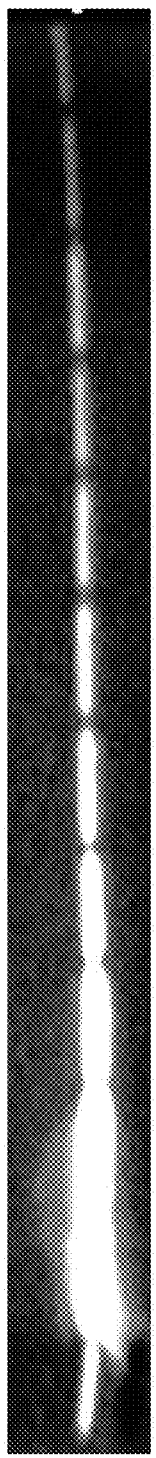
FIG. 5A is an image of a three-fold serial dilution of glutathione S-transferase (GST).
Figure 5B:
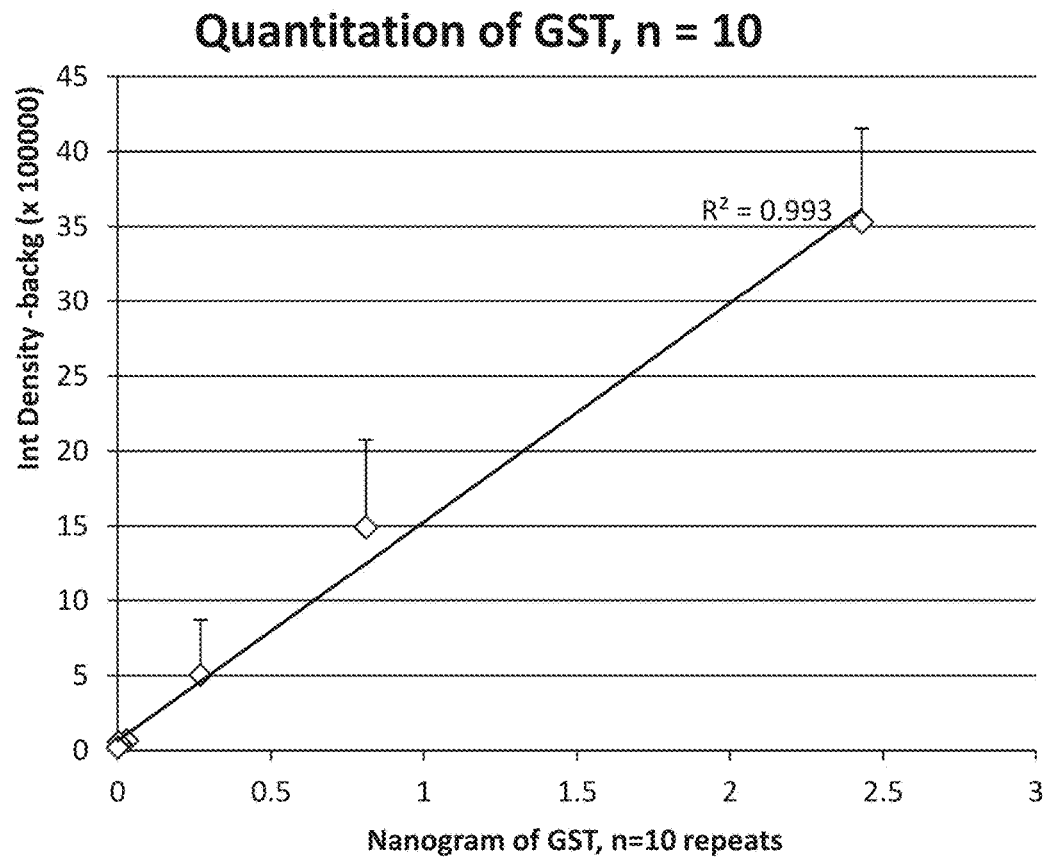
FIG. 5B is a graph of integrated intensities from individual bands across an average of 10 different Western Blots.

A three-fold serial dilution of glutathione S-transferase (GST) was used to demonstrate the dynamic range of ScanLater™ as scanned by SpectraMax® Paradigm® Multimode Detection Platform (Molecular Devices, LLC, Sunnyvale, Calif.) (see FIG. 5A). For the detection of the GST protein, biotin labeled rabbit anti-GST primary antibody was used. The ScanLater™ Eu-labeled streptavidin was used for detection. The blot was washed, dried and scanned. The system demonstrated sub-picogram detection limits of GST with over 4 logs of positive response of the signal vs. amount of GST (see FIG. 5B). FIG. 5A is an image of a GST dilution series, and FIG. 5B is a graph of integrated intensities from individual bands across an average of 10 different Western Blots.

Figure 6:
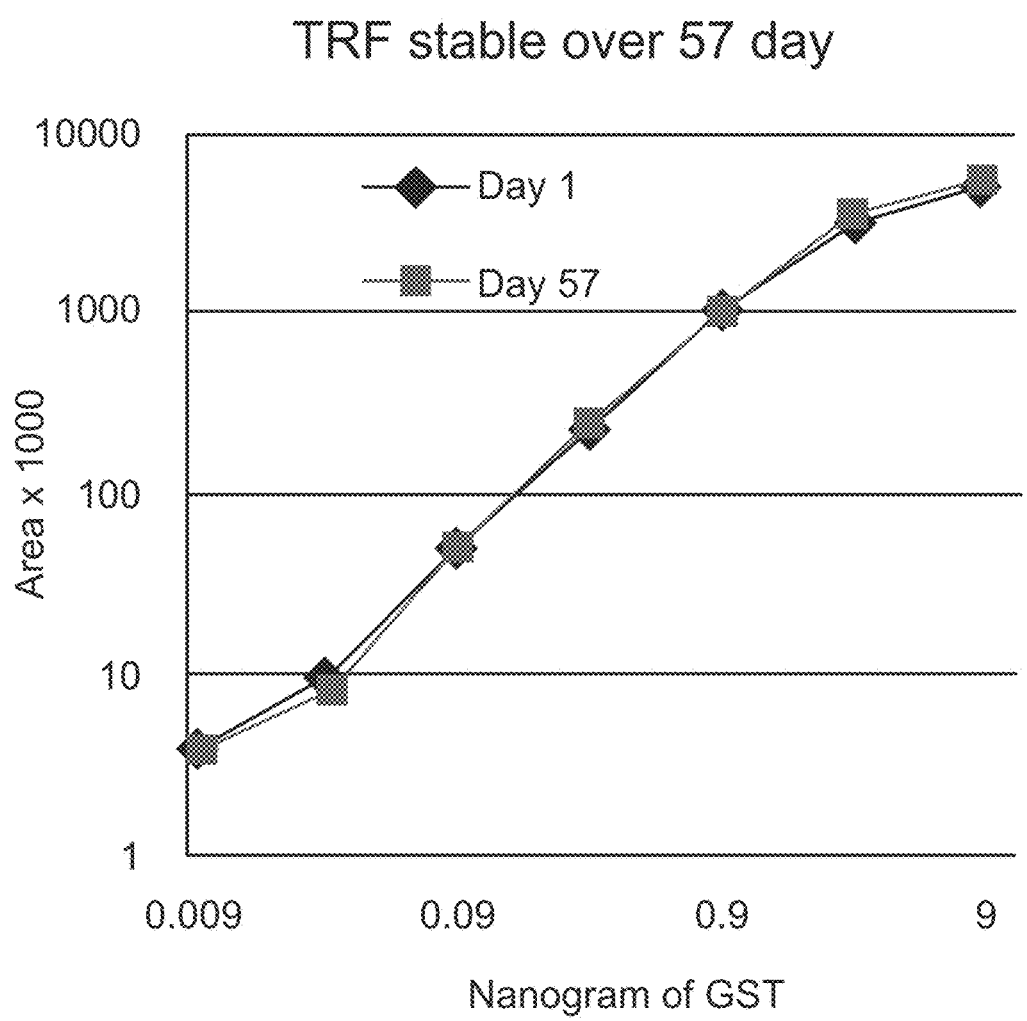
FIG. 6 is a graph showing stability of Western Blot results over time using a SpectraMax® Paradigm® reader with a ScanLater™ cartridge.

Limitations of CL and FL detection methods include signal stability. In the case of typical CL reagents, signals are stable for 5-20 minutes after which the substrate is used up and band intensity decreases. For FL, organic fluorophors are more stable when kept in appropriate conditions, but they are prone to photobleaching and signals will decay after repeated exposure to excitation light. TRF detection avoids both of these limitations and provides improved stability performance. To show long-term stability, a three-fold serial dilution of GST was used to demonstrate the signal stability over 57 days. The WB was prepared as described previously and measured immediately after preparation (Day 1) and then 57 days later after storage in a dark environment under ambient conditions. FIG. 6 is a graph showing stability of Western Blot results over time using a SpectraMax® Paradigm® reader with a ScanLater™ cartridge. The two scans were analyzed for mean band intensity over background and the results are presented in FIG. 6. No degradation of the WB or decrease in signal was observed after 57 days of storage.

Figure 7:
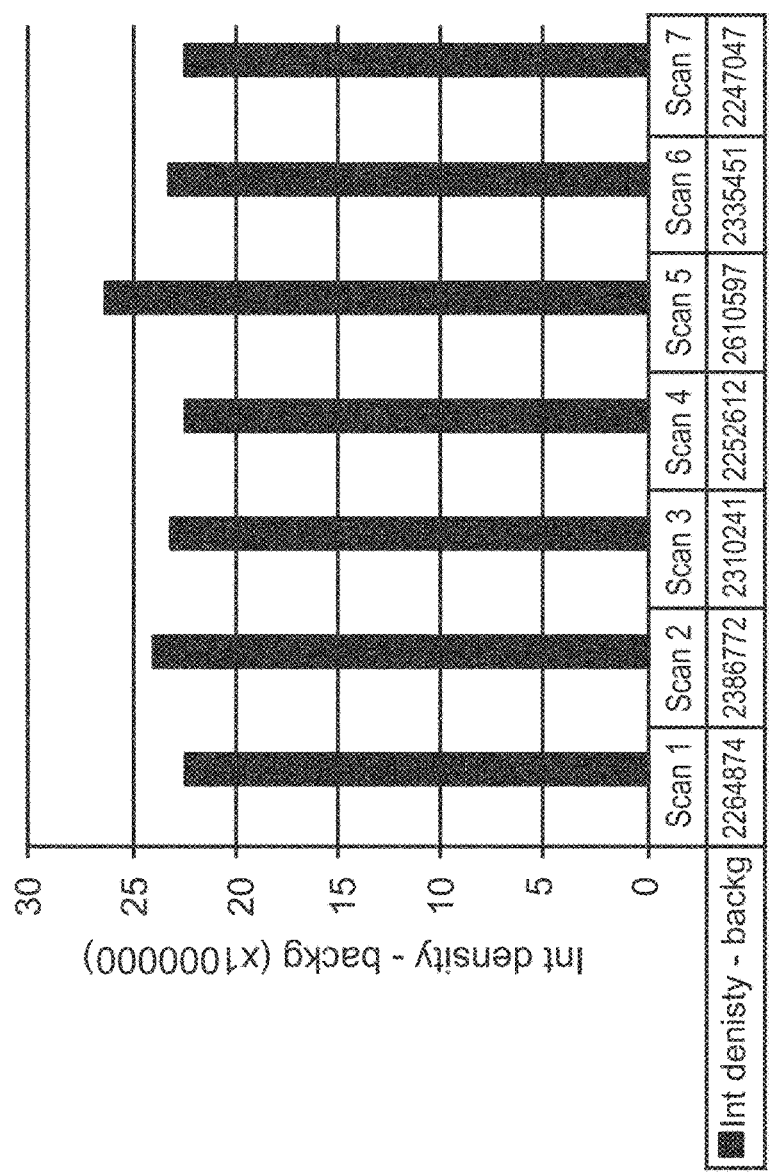
FIG. 7 is a graph showing a lack of photo-bleaching of TRF reagents after repeated scans of a single band on a Western Blot. For each scan, bars show intensity ("Int. Density").

To study the effect of photo-bleaching a WB developed with two-fold serial dilution of transferrin was subjected to repeated reads. FIG. 7 is a graph showing a lack of photo-bleaching of TRF reagents after repeated scans of a single band on a Western Blot. For each scan, bars showing integrated intensity ("Int. Density") are on the right. The average intensity from the 250 pg band was measured for each scan and the results are shown in FIG. 7. No systematic decrease in signal intensity was observed indicating that photo-bleaching of the TRF reagents was not an issue.

Multiplexing of TRF has been reported with some success. The use of Eu and Tb based probes has been demonstrated in biochemical assays using Time-Resolved Fluorescence Resonance Energy Transfer (TR-FRET) to detect two different proteins (Degorce et al. (2009) *Curr. Chem. Genomics.* 3:22-32; Bookout et al. (2000) *J. Agric. Food Chem.* 48(12):5868-5873; Hamy et al. (2001) *J. Biomol. Screen.* 6(3):179-187). In addition, there have also been reports of multiplexing with Eu and Sm, and Eu, Tb, and Sm (Bador et al. (1987) *Clin. Chem.* 33(1):48-51; Heinonen et al. (1997) *Clin. Chem.* 43(7):1142-1150). The analytical schemes for these systems use a flashlamp with a single color bandpass filter for excitation and multiple emission bandpass filters.

Figure 8:
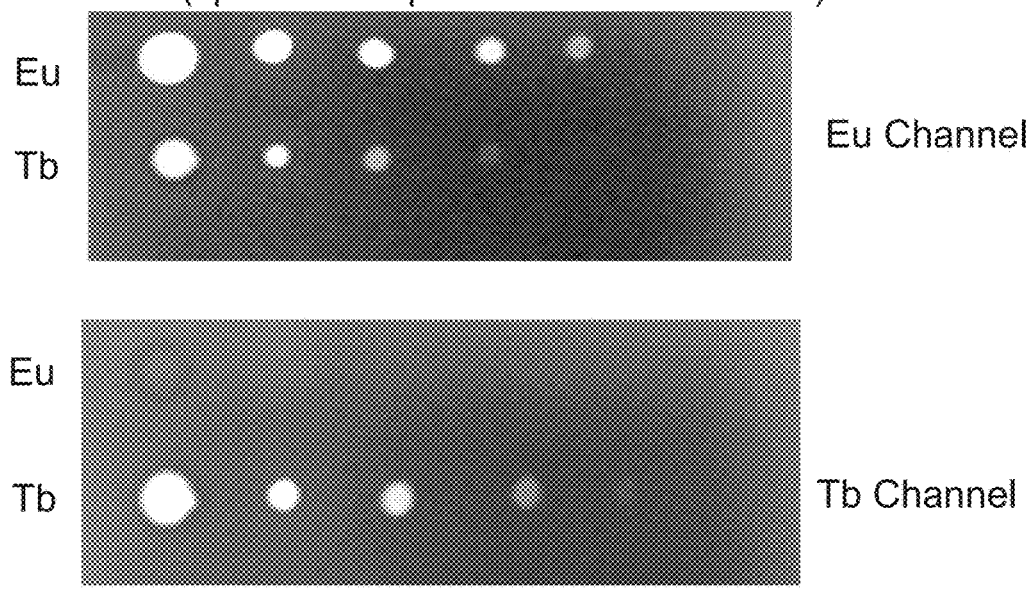
FIG. 8 shows Dot Blot results comparing cross-talk emissions between detection channels for europium (Eu) and terbium (Tb) based probes.
Figure 9:
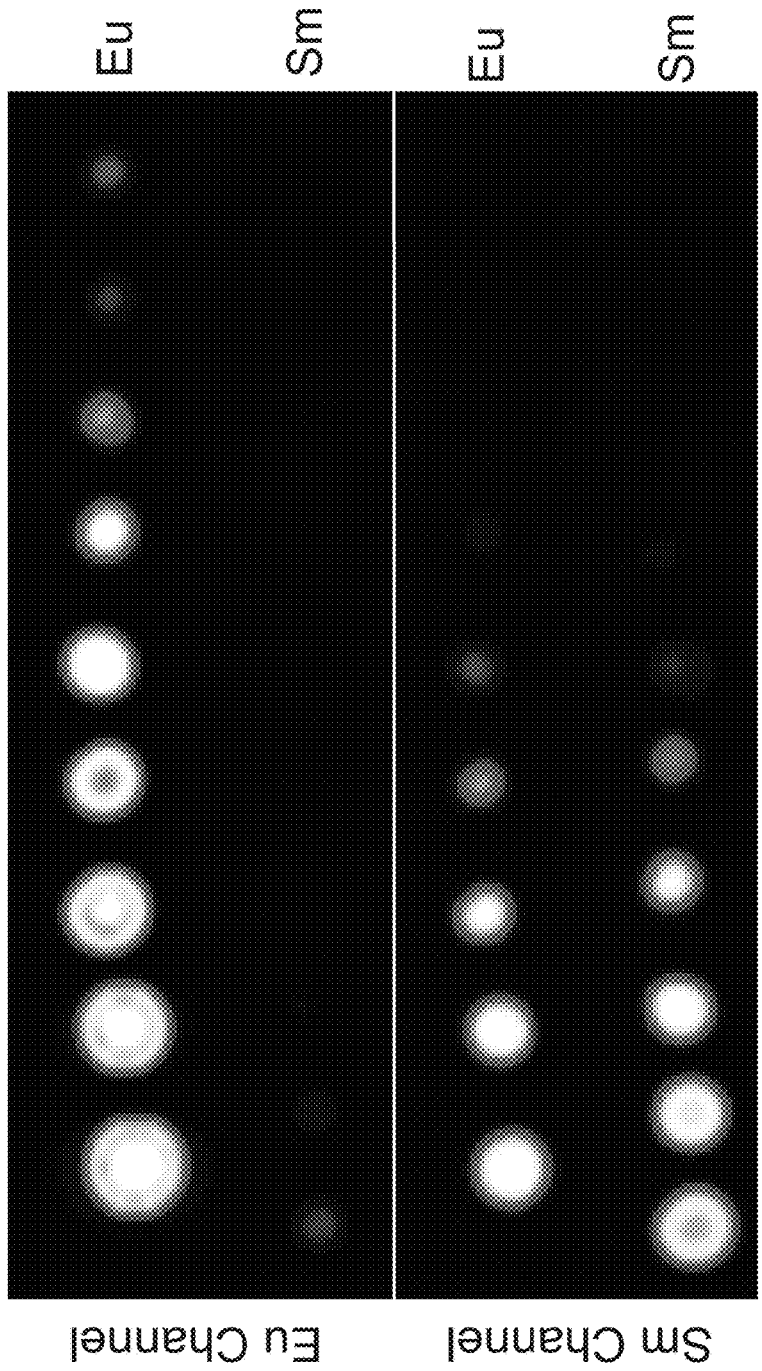
FIG. 9 shows Dot Blot results comparing cross-talk emissions between detection channels for europium (Eu) and samarium (Sm) based probes.

These systems of the prior art described above suffer from cross talk as emission from one of the lanthanides bleeds into the detection channels of the other lanthanides. In practice, good separation can be achieved in only one of the ratios because of the abundance of emission peaks in the lanthanide spectrum. For example, with Eu and Tb there is minimal Eu signal in the Tb channel, but the Tb cross talk into the Eu channel can be as high as 10%. Eu and Sm are reversed where there is no Sm cross talk into the Eu channel, but significant (>10%) Eu cross talk into the Sm channel. This limits the utility of these methods to having only one truly sensitive channel, while the other is limited by background signal from the second species. Examples of these for Eu, Tb, and Sm dot blots are shown in FIG. 8 and FIG. 9. FIG. 8 shows Dot Blot results comparing cross-talk emissions between detection channels for europium (Eu) and terbium (Tb) based probes. FIG. 9 shows Dot Blot results comparing cross-talk emissions between detection channels for europium (Eu) and samarium (Sm) based probes.

As described elsewhere herein, the present invention concerns a novel method to multiplex long lifetime fluorescent dyes using TRF detection. We used a combination of spectral and temporal differences in fluorescence emission to enhance the ability to separate signals in an assay from multiple dyes. In some embodiments, this was reduced to practice with the combination of Ruthenium (Ru) and Europium (Eu) labels in a multiplexed Western Blot detection scheme, but also has applications to immunoassays, protein arrays, and other multiplexed biological assays. Ru has been used as a dye for detection of proteins, DNA, and other compounds and its long lifetime has been used to create analytical systems that reject shorter lifetime signals (Demas et al. (1999) *Anal. Chem.* 71(23):793A-800A; Berggren et al. (1999) *Anal. Biochem.* 276(2):129-143; Ullmer et al. (2012) *Br. J. Pharmacol.* 167(7):1448-1466). However, there have been no reports of combining Ru and Eu or other very long lifetime lanthanides in a multiplexed system.

The solution we developed exploits both time-domain and wavelength domain differences between TRF dyes to reduce cross talk to below 1%, and more particularly to below 0.01%. Temporal Separation: Ru, whose half-life is ~1 μsec is detected with shorter time integration (2 μsec); Eu, whose half-life is ~800 μsec, is detected with longer time integration (1000 μsec). Spectral Separation: Ru is excited at 470 nm and detected at 624 nm; Eu is excited at 370 nm and detected at 616 nm.

Figure 10:
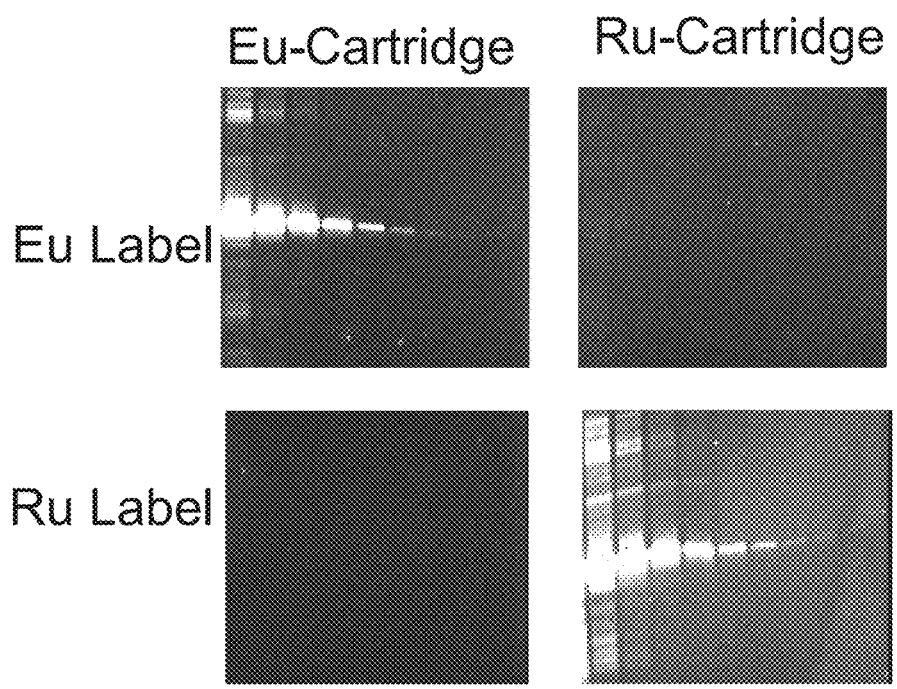
FIG. 10 shows Western Blot results of a GST dilution series comparing cross-talk emissions between detection channels with europium (Eu) and ruthenium (Ru) based probes; these scans were obtained with cartridges using laser diode excitation.

FIG. 10 shows Western Blot results of a GST dilution series comparing cross-talk emissions between detection channels with europium (Eu) and ruthenium (Ru) based probes. These scans were obtained with cartridges using laser diode excitation.

Figure 11:
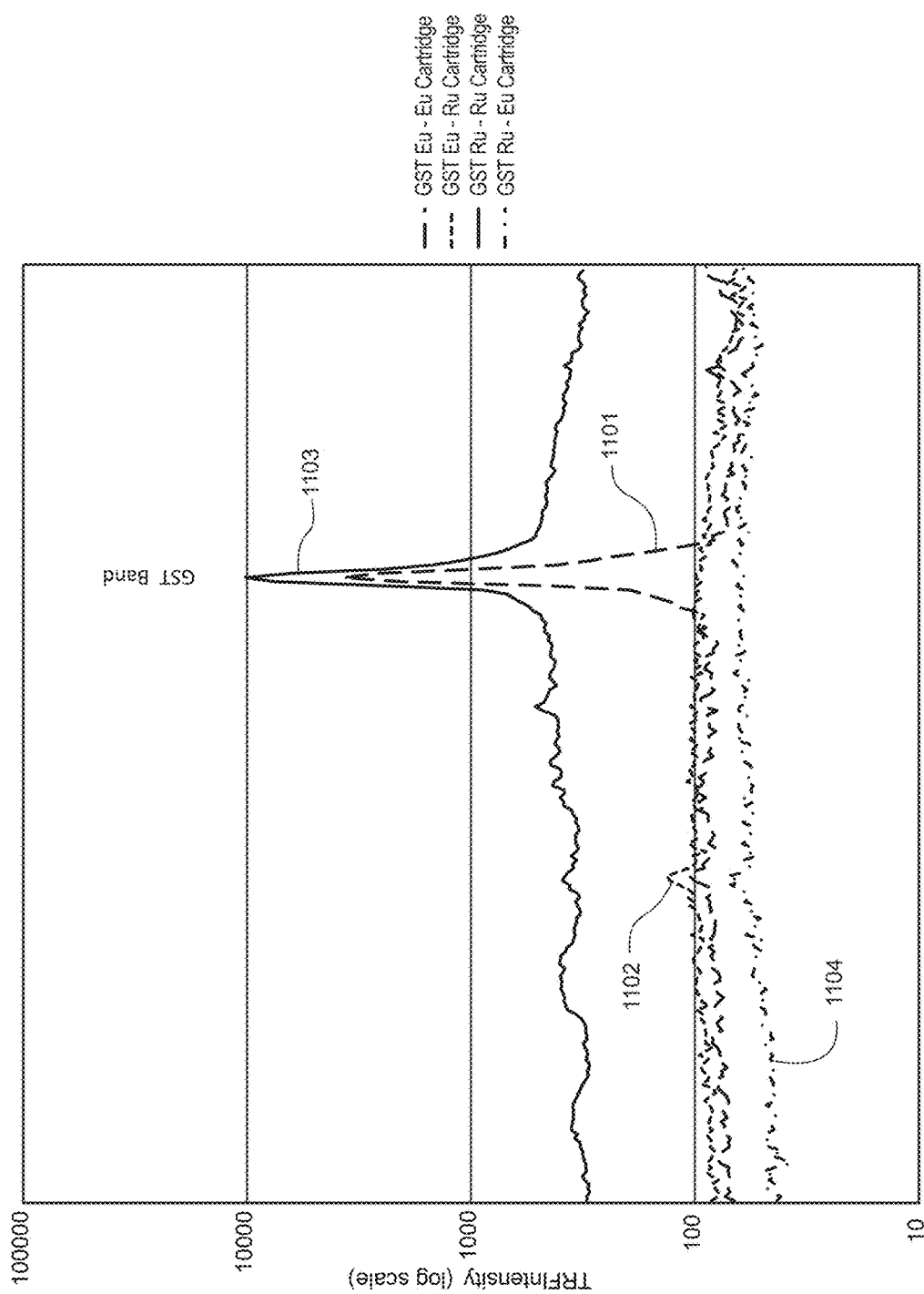
FIG. 11 is a graph showing averaged Line Scans through lanes on the Western Blots shown in FIG. 10; the line scan for the GST Eu-Eu Cartridge is labeled 1101, the line scan for the GST Eu-Ru Cartridge is labeled 1102, the line scan for the GST Ru-Ru Cartridge is labeled 1103, and the line scan for the GST Ru-Eu Cartridge is labeled 1104.

FIG. 11 is a graph showing averaged Line Scans through lanes on the Western Blots shown in FIG. 10. The line scan for the GST Eu-Eu Cartridge is labeled 1101, the line scan for the GST Eu-Ru Cartridge is labeled 1102, the line scan for the GST Ru-Ru Cartridge is labeled 1103, and the line scan for the GST Ru-Eu Cartridge is labeled 1104.

These results were obtained with two different cartridges in a SpectraMax® Paradigm® reader, but can be extended to a single cartridge that works in both SpectraMax® Paradigm® and SpectraMax® i3 Multi-Mode Microplate Reader Detection Platform systems (Molecular Devices, LLC, Sunnyvale, Calif.).

It will be understood that one or more of the processes, sub-processes, and process steps described herein may be performed by hardware, firmware, software, or a combination of two or more of the foregoing, on one or more electronic or digitally-controlled devices. The software may reside in a software memory (not shown) in a suitable electronic processing component or system such as, for example, the computing device 236 schematically depicted in FIG. 2. The software memory may include an ordered listing of executable instructions for implementing logical functions (that is, "logic" that may be implemented in digital form such as digital circuitry or source code, or in analog form such as an analog source such as an analog electrical, sound, or video signal). The instructions may be executed within a processing module, which includes, for example, one or more microprocessors, general purpose processors, combinations of processors, digital signal processors (DSPs), or application specific integrated circuits (ASICs). Further, the schematic diagrams describe a logical division of functions having physical (hardware and/or software) implementations that are not limited by architecture or the physical layout of the functions. The examples of systems described herein may be implemented in a variety of configurations and operate as hardware/software components in a single hardware/software unit, or in separate hardware/software units.

The executable instructions may be implemented as a computer program product having instructions stored therein which, when executed by a processing module of an electronic system (e.g., the computing device 236 in FIG. 2), direct the electronic system to carry out the instructions. The computer program product may be selectively embodied in any non-transitory computer-readable storage medium for use by or in connection with an instruction execution system, apparatus, or device, such as a electronic computer-based system, processor-containing system, or other system that may selectively fetch the instructions from the instruction execution system, apparatus, or device and execute the instructions. In the context of this disclosure, a computer-readable storage medium is any non-transitory means that may store the program for use by or in connection with the instruction execution system, apparatus, or device. The non-transitory computer-readable storage medium may selectively be, for example, an electronic, magnetic, optical, electromagnetic, infrared, or semiconductor system, apparatus, or device. A non-exhaustive list of more specific examples of non-transitory computer readable media include: an electrical connection having one or more wires (electronic); a portable computer diskette (magnetic); a random access memory (electronic); a read-only memory (electronic); an erasable programmable read only memory such as, for example, flash memory (electronic); a compact disc memory such as, for example, CD-ROM, CD-R, CD-RW (optical); and digital versatile disc memory, i.e., DVD (optical). Note that the non-transitory computer-readable storage medium may even be paper or another suitable medium upon which the program is printed, as the program can be electronically captured via, for instance, optical scanning of the paper or other medium, then compiled, interpreted, or otherwise processed in a suitable manner if necessary, and then stored in a computer memory or machine memory.

It will also be understood that the term "in signal communication" as used herein means that two or more systems, devices, components, modules, or sub-modules are capable of communicating with each other via signals that travel over some type of signal path. The signals may be communication, power, data, or energy signals, which may communicate information, power, or energy from a first system, device, component, module, or sub-module to a second system, device, component, module, or sub-module along a signal path between the first and second system, device, component, module, or sub-module. The signal paths may include physical, electrical, magnetic, electromagnetic, electrochemical, optical, wired, or wireless connections. The signal paths may also include additional systems, devices, components, modules, or sub-modules between the first and second system, device, component, module, or sub-module.

More generally, terms such as "communicate" and "in . . . communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A method for multiplexed time-resolved fluorescence (TRF) detection, the method comprising the steps of:
    a) providing a sample on a sample support, the sample comprising a first fluorescent label bound to a first analyte and a second fluorescent label bound to a second analyte, wherein the first fluorescent label has a first fluorescence emission lifetime, a first excitation wavelength, and a first emission wavelength, and the second fluorescent label has a second fluorescence emission lifetime, a second excitation wavelength different from the first excitation wavelength, and a second emission wavelength, and the first fluorescence emission lifetime is at least 3 times longer than background fluorescence emission lifetimes;
    b) exciting the first fluorescent label with a first excitation light having the first excitation wavelength, whereby the first fluorescent label emits a first detection signal having the first emission wavelength;
    c) exciting, thereafter, the second fluorescent label with a second excitation light having the second excitation wavelength, whereby the second fluorescent label emits a second detection signal having the second emission wavelength;
    d) directing the first detection signal through an emission filter to filter the first detection signal, and then to a detector;
    e) directing the second detection signal through the emission filter to filter the second detection signal, and then to the detector;
    f) measuring intensity of the first detection signal at the detector, wherein the intensity of the first detection signal is correlated with the amount of the first analyte in the sample; and
    g) measuring intensity of the second detection signal at the detector, wherein the intensity of the second detection signal is correlated with the amount of the second analyte in the sample, and wherein:
    the second fluorescence emission lifetime is at least 5 times longer than the first fluorescence emission lifetime;
    the first fluorescent label is selected from a first group consisting of transition metal chelates of ruthenium (Ru(II)), osmium (Os(II)), and rhenium (Re(I));
    the second fluorescent label is selected from a second group consisting of lanthanide chelates of samarium (Sm(III)), dysprosium (Dy(III)), europium (Eu(III)), and terbium (Tb(III)), wherein the first fluorescent label and the second fluorescent label are each selected from the first group and second group respectively, rather than both being selected from the same group.

2. The method of claim 1, wherein the second fluorescence emission lifetime is at least 100 times longer than the first fluorescence emission lifetime.

3. The method of claim 1, wherein the second fluorescence emission lifetime is at least 1,000 times longer than the first fluorescence emission lifetime.

4. The method of claim 1, wherein the second fluorescence emission lifetime is in a range of 100 μs to 1 ms.

5. The method of claim 1, wherein the first fluorescence emission lifetime is in a range of 0.1 μs to 10 μs.

6. The method of claim 1, wherein the first fluorescent label and/or the second fluorescent label have a Stokes shift of greater than 20 nm.

7. The method of claim 1, wherein the first fluorescent label and/or the second fluorescent label have a Stokes shift of greater than 50 nm.

8. The method of claim 1, wherein the first fluorescent label and/or the second fluorescent label have a Stokes shift of greater than 100 nm.

9. The method of claim 1, wherein the first analyte and the second analyte comprise proteins.

10. The method of claim 9, wherein the first analyte and the second analyte comprise membrane-bound proteins.

11. The method of claim 1, wherein prior to step (a) the sample is prepared according to the following steps:
    a) contacting the sample with:
        i) a first antibody that specifically binds the first analyte;
        ii) a second antibody that specifically binds the second analyte;
        iii) a first fluorescent antibody conjugate that specifically binds the first antibody, wherein the first fluorescent antibody conjugate comprises the first fluorescent label;
        iv) a second fluorescent antibody conjugate that specifically binds the second antibody, wherein the second fluorescent antibody conjugate comprises the second fluorescent label; and
    b) incubating the sample under conditions and for a time sufficient to allow the antibodies and the antibody conjugates to form immunocomplexes.

12. The method of claim 1, comprising contacting the sample with a first antibody that specifically binds the first analyte and a second antibody that specifically binds the second analyte,
    wherein the first fluorescent label is attached directly to the first antibody, or the second fluorescent label is attached directly to the second antibody, or both of the foregoing.

13. The method of claim 1, further wherein:
    i) the sample further comprises at least one additional fluorescent label bound to an additional analyte, wherein the additional fluorescent label has a label-specific excitation wavelength, a label-specific emission wavelength, and a label-specific fluorescence emission lifetime which is at least 3 times longer than background emission lifetimes;

ii) the additional fluorescent label is excited with a label-specific excitation light having the label-specific excitation wavelength, whereby the additional fluorescent label emits a label-specific detection signal having the label-specific emission wavelength; and iii) intensity of the label-specific detection signal is measured, wherein the intensity of the label-specific detection signal is positively correlated with the amount of the additional analyte in the sample;

wherein the first fluorescence emission lifetime, the second fluorescence emission lifetime, and the label-specific fluorescence emission lifetime are each at least an order of magnitude different from one another.

14. The method of claim 13, wherein the at least one additional fluorescent label bound to an additional analyte comprises a plurality of different fluorescent labels bound to different analytes.

15. The method of claim 1, wherein the first analyte is a reference protein and the second analyte is an unknown protein, further wherein the second detection signal is normalized to the first detection signal.

16. The method of claim 1, wherein the first analyte is a protein and the second analyte is a modified version of the protein, further wherein the ratio of modified protein to unmodified protein is calculated.

17. The method of claim 16, wherein the modified version of the protein is a phosphorylated version of the protein.

18. The method of claim 1, wherein:
the emission filter comprises a first emission filter a second emission filter;
directing the first detection signal through the emission filter comprises directing the first detection signal through the first emission filter; and
directing the second detection signal through the emission filter comprises directing the second detection signal through the second emission filter.

19. The method of claim 18, wherein:
the detector comprises a first detector and a second detector;
measuring the intensity of the first detection signal at the detector comprises measuring the intensity of the first detection signal at the first detector; and
measuring intensity of the second detection signal at the detector comprises measuring the intensity of the second detection signal at the second detector.

20. The method of claim 1, further comprising:
separating the first detection signal from the second detection signal using a combination of spectral and temporal differences in the first and second fluorescence emissions induced respectively by the first and second excitation lights.

21. The method of claim 20, wherein the separating comprises integrating the first detection signal of the first fluorescence at the first emission wavelength for a shorter time period than the second detection signal of the second fluorescence at the second emission wavelength.

* * * * *